US007531355B2

(12) United States Patent
Rodríguez et al.

(10) Patent No.: US 7,531,355 B2
(45) Date of Patent: May 12, 2009

(54) METHODS AND COMPOSITIONS FOR SMOOTH MUSCLE RECONSTRUCTION

(75) Inventors: Larissa V. Rodríguez, Los Angeles, CA (US); Ben Wu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 403 days.

(21) Appl. No.: 11/192,753

(22) Filed: Jul. 29, 2005

(65) Prior Publication Data

US 2007/0025972 A1 Feb. 1, 2007

(51) Int. Cl.
*C12N 5/00* (2006.01)
(52) U.S. Cl. .................. 435/377; 435/325; 435/375
(58) Field of Classification Search .................. None
See application file for complete search history.

(56) References Cited

U.S. PATENT DOCUMENTS

| 4,443,546 | A | 4/1984 | Stemerman et al. |
| 5,605,687 | A | 2/1997 | Lee |
| 5,786,207 | A | 7/1998 | Katz et al. |
| 6,153,432 | A | 11/2000 | Halvorsen et al. |
| 6,391,297 | B1 | 5/2002 | Halvorsen |
| 6,426,222 | B1 | 7/2002 | Patat et al. |
| 6,429,013 | B1 | 8/2002 | Halvorsen et al. |
| 6,555,374 | B1 | 4/2003 | Gimble et al. |
| 6,777,231 | B1 | 8/2004 | Katz et al. |
| 6,841,150 | B2 | 1/2005 | Halvorsen et al. |
| 6,866,842 | B1 | 3/2005 | Chancellor et al. |
| 2001/0033834 | A1 | 10/2001 | Wilkison et al. |
| 2002/0102728 | A1* | 8/2002 | Moutsatsos et al. .......... 435/455 |
| 2002/0115647 | A1 | 8/2002 | Halvorsen et al. |
| 2003/0125293 | A1 | 7/2003 | Cheatham et al. |
| 2003/0147831 | A1* | 8/2003 | Marko .................... 424/70.14 |
| 2003/0152558 | A1 | 8/2003 | Luft et al. |
| 2003/0161816 | A1 | 8/2003 | Fraser et al. |
| 2003/0166278 | A1 | 9/2003 | Gimble et al. |
| 2003/0180269 | A1 | 9/2003 | Hariri |
| 2004/0092011 | A1 | 5/2004 | Wilkison et al. |
| 2004/0166096 | A1 | 8/2004 | Kolkin et al. |
| 2004/0193274 | A1* | 9/2004 | Trieu .................... 623/17.16 |
| 2004/0229351 | A1 | 11/2004 | Rodriguez et al. |
| 2005/0076396 | A1 | 4/2005 | Katz et al. |

FOREIGN PATENT DOCUMENTS

| WO | WO 97/18299 | 5/1997 |
| WO | WO 97/39104 | 10/1997 |
| WO | WO 97/40137 | 10/1997 |
| WO | WO 97/41208 | 11/1997 |
| WO | WO 98/04682 | 2/1998 |
| WO | WO 98/20731 | 5/1998 |
| WO | WO 98/32333 | 7/1998 |
| WO | WO 98/51317 | 11/1998 |
| WO | WO 99/01145 | 1/1999 |
| WO | WO 99/02654 | 1/1999 |
| WO | WO 99/03973 | 1/1999 |
| WO | WO 99/11789 | 3/1999 |
| WO | WO 99/28444 | 6/1999 |
| WO | WO 00/53795 | 9/2000 |
| WO | WO 01/62901 A2 | 8/2001 |

OTHER PUBLICATIONS

De Ugarte DA et al. 2003. Differential expression of stem cell mobilization-associated molecules on multi-lineage cells from adipose tissue and bone marrow. Immunol Lett 89: 267-270.*
Charbord P et al. 2000. Analysis of the microenvironment necessary for engraftment: role of the vascular smooth muscle-like stromal cells. J Hematotherapy Stem Cell Res 9: 935-943.*
Ashjian, P.H. et al. "In Vitro Differentiation of Human Processed Lipoaspirate Cells into Early Neural Progenitors" *Plast. Reconstr. Surg.* (2003) 111:1922-1931.
Atala, A. "Tissue engineering for the Replacement of organ function in the genitourinary system" *Am J. Transplan.* (2004) 4(Suppl. 6):58-73.
Atala, A. et al. "Endoscopic treatment of vesicoureteral reflux with a chondrocyte-alginate suspension" *J. Urol.* (Aug. 1994) 152:641-643.
Balmforth, J. and L.D. Cardozo "Trends toward less invasive treatment of female stress urinary incontinence" *Urology* (2003) 62(Suppl. 4A):52-60.
Bent, A.E. et al. "Treatment of Intrinsic Sphincter Deficiency Using Autologous Ear Chondrocytes as a Bulking Agent" *Neurourio. Urodynam.* (2001) 20:157-165.
Burris, T.P. et al. "A Novel Method for Analysis of Nuclear Receptor Function at Natural Promoters: Peroxisome Proliferator-Activated Receptor γ Agonist Actions on aP2 Gene Expression Detected Using Branched DNA Messenger RNA Quantitation" *Mol. Endocrinol.* (1999) 13:410-417.
Cai, J. et al. "In search of 'stemness'" *Exp. Hematol.* (2004) 32:585-598.
Camargo, F.D. et al. "Single hematopoietic stem cells generate skeletal muscle through myeloid intermediates" *Nat. Med.* (Dec. 2003) 9(12):1520-1527.

(Continued)

*Primary Examiner*—Lora E Barnhart
(74) *Attorney, Agent, or Firm*—Antoinette F. Konski; Foley & Lardner LLP

(57) ABSTRACT

This invention also provides a purified or isolated population of ADSCs that can differentiate into a cell of the leiomyogenic lineage, e.g., smooth muscle or skeletal muscle. In yet another aspect, the population additionally can be differentiated into a lineage selected from the group consisting of osteogenic, adipogenic, chondrogenic, myogenic and neuronal. This invention further provides a composition comprising a substantially homogeneous expanded population of smooth muscle cells. This invention provides a composition comprising a substantially homogeneous expanded population of skeletal muscle cells. Also provided herein is an isolated composition comprising a purified adipose-derived stem cell (ADSC) or progeny of said ADSC and an effective amount of laminin or heparin, effective to induce leiomyogenic differentiation. Diagnositic and therapeutic uses for these compositions are provided herein.

9 Claims, 9 Drawing Sheets

OTHER PUBLICATIONS

Cannon, T.W. et al. "Improved sphincter contractility after allogenic muscle-derived progenitor cell injection into the denervated rat urethra" *Urology* (2003) 62:958-963.

Corcos, J. and C. Fournier "Periurethral collagen injection for the treatment of female stress urinary incontinence: 4-year follow-up results" *Urology* (1999) 54:815-818.

Erickson, G.R. et al. "Chondrogenic Potential of Adipose Tissue-Derived Stromal Cells in Vitro and in Vivo" *Biochem Biophys Res Commun.* (Jan. 18, 2002) 290(2):763-769.

Gronthos, S. et al. "Surface Protein Characterization of Human Adipose Tissue-Derived Stromal Cells" *J. Cell. Phys.* (2001) 189:54-63.

Halvorsen, Y.-D. C. et al. "Thiazolidinediones and Glucocorticoids Synergistically Induce Differentiation of Human Adipose Tissue Stromal Cells: Biochemical, Cellular, and Molecular Analysis" *Metabolism* (Apr. 2001) 50(4):407-413.

Halvorsen, Y.-D. C. et al. "Extracellular Matrix Mineralization and Osteoblast Gene Expression by Human Adipose Tissue-Derived Stromal Cells" *Tissue Eng.* (2001) 7(6):729-741.

Harp , J.B. et al. "Differential Expression of Signal Transducers and Activators of Transcription during Human Adipogenesis" *Biochem Biophys Res Commun* (2001) 281:907-912.

Hauner, H. et al. "Glucocorticoids and Insulin Promote the Differentiation of Human Adipocyte Precursor Cells into Fat Cells" *J. Clin. Endocrinol. Metabol.* (1987) 64(4):832-835.

Katz, A.J. et al. "Emerging Approaches to the Tissue Engineering of Fat" *Clin. Plast. Surg.* (Oct. 1999) 26(4):587-603.

Kuo, H.-C. "Effects of Vaginal Trauma and Oophorectomy on the Continence Mechanism in Rats" *Urol. Int.* (2002) 69:36-41.

Lee, J.Y. et al. "The effects of periurethal muscle-derived stem cell injection on leak point pressure in a rat model of stress urinary incontinence" *Int. Urogynecol. J.* (2003) 14:31-37.

Lin, A.S. et al. "Effect of stimulated birth trauma on the urinary continence mechanism in the rat" *Urology* (1998) 52:143-151.

Lin, H.-K. et al. "Characterization of neuropathic bladder smooth muscle cells in culture" *J. Urol.* (Mar. 2004) 171:1348-1352.

McFarland, D.C. "Preparation of pure cell cultures by cloning" *Meths. Cell Sci.* (2000) 22:63-66.

Matsuzaki, Y. et al. "Unexpectedly Efficient Homing Capacity of Purified Murine Hematopoietic Stem Cells" *Immunity* (Jan. 2004) 20:87-93.

Morizono, K. et al. "Multilineage Cells from Adipose Tissue as Gene Delivery Vehicles" *Hum. Gene Ther.* (Jan. 1, 2003) 14:59-66.

Mizuno, H. et al. "Myogenic Differentiation by Human Processed Lipoaspirate Cells" *Plast. Reconstr. Surg.* (2002) 109:199-209.

Oberpenning, F. et al. "De novo reconstitution of a functional mammalian urinary bladder by tissue engineering" *Nat. Biotech.* (Feb. 1999) 17:149-155.

Olson, M.E. et al. "Evaluation of autologous fat implantation in the rat urinary bladder submucosa" *Urology* (1998) 52:915-919.

Pehrson, R. et al. "Effects of Tramadol on Rat Detrusor Overactivity Induced by Experimental Cerebral Infarction" *Eur. Urol.* (2003) 44:495-499.

Presnell, S.C. et al. "Stem cells in adult tissues" *Sem. Cell Develop. Biol.* (2002) 13:369-376.

Resplande, J. et al. "Long-term effect of ovariectomy and simulated birth trauma on the lower urinary tract of female rats" *J. Urol.* (Jul. 2002) 168:323-330.

Saladin, R. et al. "Differential Regulation of Peroxisome Proliferator Activated Receptor γ1 (PPARγ1) and PPARγ2 Messenger RNA Expression in the Early Stages of Adipogenesis" *Cell Growth & Diff.* (Jan. 1999) 10:43-48.

Sen, A. et al. "Adipogenic Potential of Human Adipose Derived Stromal Cells From Multiple Donors is Heterogeneous" *J Cell. Biochem.* (2001) 81:312-319.

Sievert, K.-D. et al. "The effect of simulated birth trauma and/or ovariectomy on rodent continence mechanism. Part I. Functional and structural change" *J. Urol.* (Jul. 2001) 166:311-317.

Soda, R. and M. Tavassoli "Adipocyte Stem Cell: A Brief Review" *Int. J Cell Cloning* (1983) 1:79-84.

Sprangrude, G.J. "Stem Cells and Tissue Regeneration. When is a Stem Cell Really a Stem Cell?" *Bone Marrow Transplan.* (2003) 32:S7-S11.

Stenzl, A. et al. "Reconstruction of the lower urinary tract using autologous muscle transfer and cell seeding: current status and future perspectives" *World J. Urol.* (2000) 18:44-50.

Strasser, H. et al. "Urinary incontinence in the elderly and age-dependent apoptosis of rhabdosphincter cells" *Lancet* (Sep. 11, 1999) 354:918-919.

Suzuki, A. et al. "Prospective Isolation of Multipotent Pancreatic Progenitors Using Flow-Cytometric Cell Sorting" *Diabetes* (Aug. 2004) 53:2143-2152.

Sylvester, K.G. and M.T. Longaker "Stem Cells" *Arch. Surg* (Jan. 2004) 139:93-99.

Timmermans, F. et al. "Stem Cells for the Heart, Are We There Yet?" *Cardiology* (2003) 100:176-185.

Trockman, B.A. and G.E. Leach "Surgical Treatment of Intrinsic Urethral Dysfunction: Injectable (Fat)" *Urol. Clin. North Am.* (Aug. 1995) 22(3):665-671.

Weissman, I.L. "Stem Cells: Units of Development, Units of Regeneration, and Units in Evolution" *Cell* (Jan. 7, 2000) 100:157-168.

Yokoyama, T. et al. "Myoblast therapy for stress urinary incontinence and bladder dysfunction" *World J. Urol.* (2000) 18:56-61.

Yokoyama, T. et al. "Persistence and survival of autologous muscle derived cells versus bovine collagen as potential treatment of stress urinary incontinence" *J. Urol.* (Jan. 2001) 165:271-276.

Yokoyama, T. et al. "Gene Therapy and Tissue Engineering for Urologic Dysfunction: Status and Prospects" *Mol. Urol.* (2001) 5(2):67-70.

Yoon, Y.-S. et al. "Clonally Expanded Novel Multipotent Stem Cells from Human Bone Marrow Regenerate Myocardium After Myocardial Infarction" *J. Clin. Invest.* (Feb. 2005) 115(2):326-338.

Zhou, L. et al. "Analysis of the pattern of gene expression during human adipogenesis by DNA microarray" *Biotechnol. Techniques* (1999) 13:513-517.

Zipori, D. "The Nature of stem cells: state rather than entity" *Nature Reviews/Genetics* (Nov. 2004) 5:873-878.

Zuk, P.A. et al. "Multilineage Cells from Human Adipose Tissue: Implications for Cell-Based Therapies" *Tissue Eng.* (2001) 7(2):211-228.

Zuk, P.A. et al. "Human Adipose Tissue Is a Source of Multipotent Stem Cells" *Mol. Biol. Cell* (Dec. 2002) 13:4279-4295.

Grinnell, F. et al. "Differences in the Regulation of Fibroblast Contraction of Floating Versus Stressed Collagen Matrices" (1999) *J. Biol. Chem.* 274(2):918-923.

Lee, J.Y. et al. "The effects of periurethral muscle-derived stem cell injection on leak point pressure in a rat model of stress urinary incontinence" (2003) *Int Urogynecol J* 14(1):31-37.

Strasser, H. et al. "Stammzelltherapie der Haminkontinenz" (2004) *Der Urologe* [A] 43:1237-1241.

Charbord et al. (2000) "Analysis of the Microenvironment Necessary for Engraftment: Role of the Vascular Smooth Muscle-like Stromal Cells" Journal of Hematotherapy & Stem Cell Research 9:935-943.

* cited by examiner

FIGURE 1A
FIGURE 1B
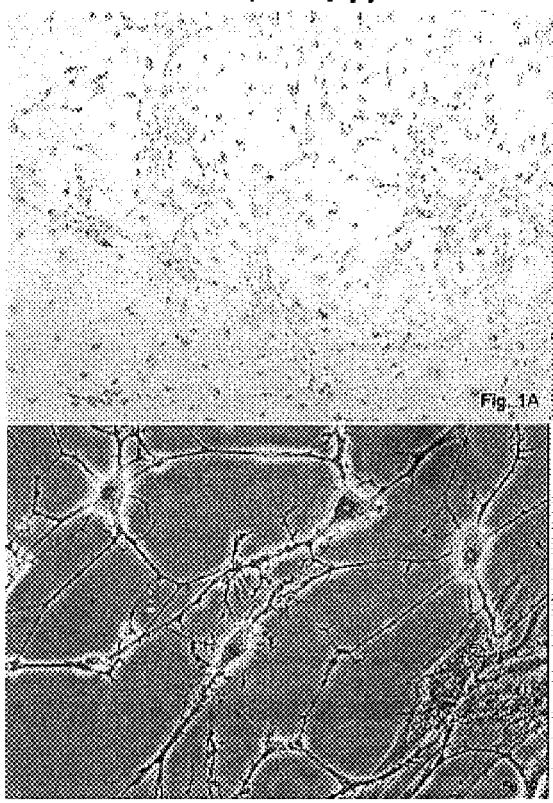
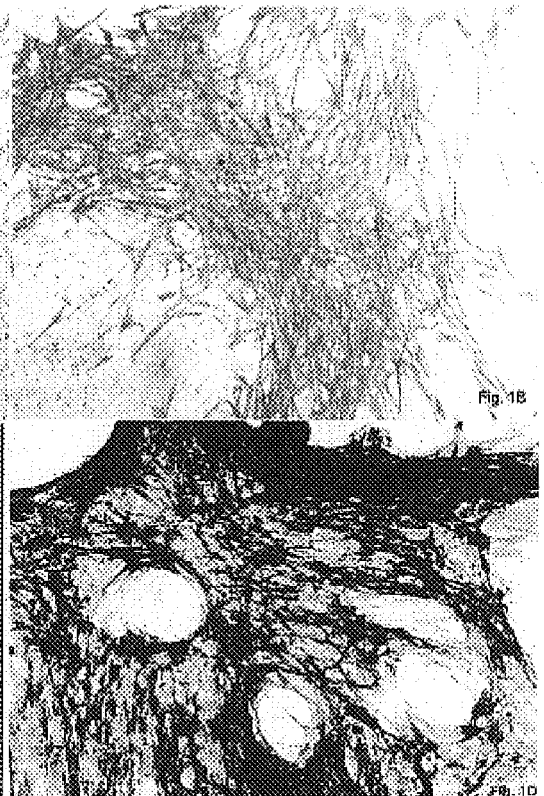
FIGURE 1C
FIGURE 1D

FIGURE 1E
FIGURE 1F
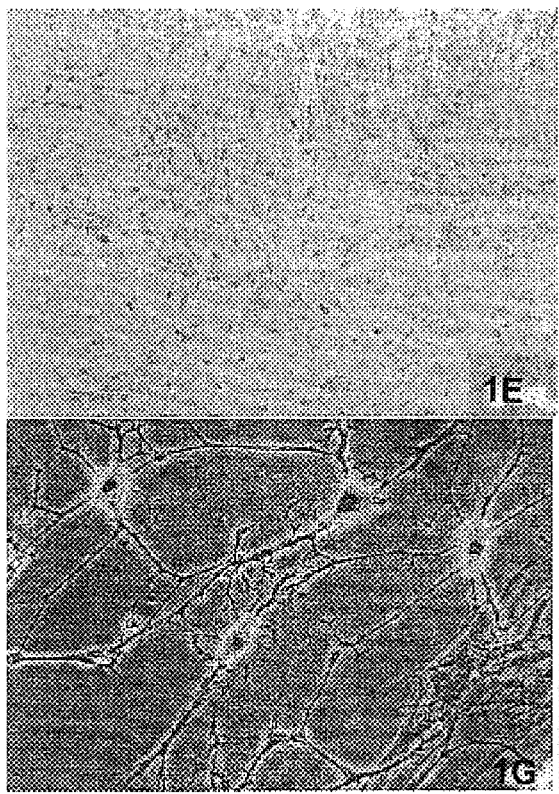
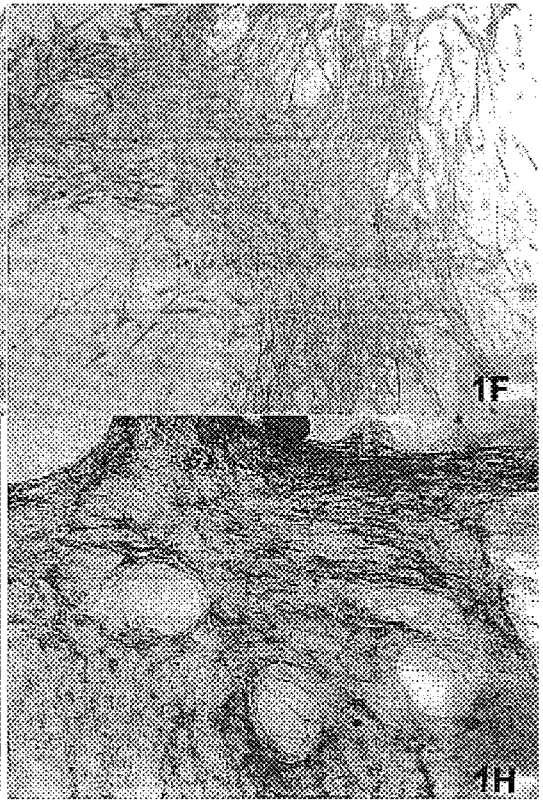
FIGURE 1G
FIGURE 1H

METHODS AND COMPOSITIONS FOR SMOOTH MUSCLE RECONSTRUCTION

STATEMENT OF GOVERNMENT SUPPORT

This invention was made with Government support of Grand No. KD076198 and HD01400 awarded by the National Institutes of Health. Accordingly, the U.S. government has certain rights in this invention.

TECHNICAL FIELD

The invention relates to methods and compositions to reconstruct smooth muscle in vivo and for in vitro assays useful in drug discovery.

BACKGROUND

Urinary incontinence and bladder disease present unmet medical needs due, in part, to the inability of current therapies to correct loss of smooth muscle function associated with these disorders. Loss of functional smooth muscle in urethra accounts for a high degree of incontinence and the bladder is itself a smooth muscle organ.

Tissue engineered grafts have been created using host bladder cells to overcome these limitations. However, the use of bladder smooth muscle (SM) cells entails limitations as well. Oberpenning et al. (1999) Nat. Biotech. 17:149. In addition to the tremendous time and materials required for their expansion, studies have shown that cells from pathologic bladders, including neurogenic bladders, retain their neurogenic features in vitro. Lin et al. (2004) J. Urol. 171:1348.

The search for an ideal cell source for tissue engineering of the lower urinary tract has remained elusive. Atala and colleagues ((2004) Am. J. Transp. 4 Suppl.6:58) reported the use of autologous bladder smooth muscle (SM) cells to augment the bladder wall, however their experiments were limited to normal animals and required extensive cell culture and expansion. Bulking therapies of the urethra for the treatment of stress urinary incontinence (SUI) have faced similar limitations. The use of chondrocytes as a cell source for injection into the urethra was described by Atala et al. (1944) J. Urol. 152:641. Chondrocytes, harvested from the ear and expanded in culture, were implanted into the urethra and subsequently transformed into a rubbery-hard cartilage structure that provided bulk to the urethra. Atala et al. (1994) supra. While the results were encouraging, the long-term continence rates obtained using chondrocyte injections were similar to those achieved using traditional bulking agents such as collagen, silicone, and others. See Balmforth et al. (2003) Urology 62:52 and Beyt et al. (2001) Neuroalo. Urodyn. 20:157. Other investigators sought to use unprocessed fat as a bulking agent for SUI on the basis that fat is readily available, easily harvested, and immuno-compatible. Trockman et al. (1995) Urol. Clin. North Am. 22:665. While initially promising, less than 30% of the injected fat remained in the urethra after 35 days due to fat necrosis and inflammation. Olson et al. (1998) Urology 52:915.

More recently, investigators have described skeletal muscle cells as a source of tissue for the treatment of SUI and bladder dysfunction. Stenzl et al. (2000) World J. Urol. 18:44; Strasser et al. (2004) Urologe A. 43:1237; Corcos et al. (1999) Urology 54:815; and Yokayama et al. (2001) Mol. Urol. 5:67. Studies using injections of skeletal muscle cells have shown that the cells can remain viable in the rat urethra for up to 30 days and for up to 6 months in the bladder of SCID mice. Yokoyama et al. (2000) World J. Urol. 18:56 and Yokoyama et al. (2001) J. Urol. 165:271. Injected cells express myotubules and fast myosin heavy chain in vivo, consistent with striated muscle differentiation. Yokoyama et al. (2001) J. Urol. 165:271. Investigators reported improved sphincter contractility and elevated leak point pressures in animal models, Cannon et al. (2003) Urology 62:958 and Lee et al. (2003) J. Pelvic Floor Dysfunction 14:31 as well as improved continence in human subjects after injection of autologous skeletal muscle cells and fibroblasts into the rhabdosphincter and urethra. Strasser et al. (2004) Urologe A 43:1237. While these studies are very exciting examples of the potential of autologous cell transplantation for tissue engineering, it is still undetermined if skeletal muscle progenitors can differentiate into functional smooth muscle (SM) cells for long term applications outside of skeletal muscle regeneration. Lee et al. (2003) J. Pelvic Floor Dysfunction 14:31 and Timmermans et al. (2003) Cardiology 100:176. Moreover, there is a clear difference between smooth muscle and skeletal muscle cells.

Three kinds of muscle are found in all vertebrates: cardiac, smooth and skeletal muscle. Skeletal muscle is also called striated muscle and is usually attached to the skeleton. Its contraction is under voluntary control. Skeletal muscle is made up of thousands of cylindrical muscle fibers. Each one of these fibers contains an array of myofibrils, mitochondria, and endoplasmic reticulum and multiple nuclei. Thus skeletal muscle cells are multinucleated. Each myofibril is made of parallel filaments. The thick filaments are composed of the protein myosin and the thin filaments of troponin and tropomyosin. The contraction of skeletal muscle is controlled by the nervous system. In this respect, it differs from smooth muscle which can contract without stimulation from the nervous system. On the other hand, smooth muscle is found on the wall of the hollow organs of the body. Its contraction reduces the size of these structures. Thus it regulates the flow of blood in the arteries, moves food boluses through the intestinal tract, expels urine from the urinary bladder, is involved in uterine contractions and regulates the flow of air though the lungs among other functions. Unlike skeletal muscle, smooth muscle is made of single, spindle-shaped cells. The cell contains myosin and actin filaments that slide against each other to produce contraction of the cell. Unlike skeletal muscle, they do not depend on motor neurons to contract. However, neurons that reach smooth muscle can stimulate it by inducing contraction or relaxation. In addition, smooth muscle cells can respond to paracrine and hormonal stimulation. The contraction of smooth muscle tends to be slower than that of striated muscle and sustained for long period of time. Therefore, smooth muscle is capable of baseline tone.

Stem cells on the other hand, possess self-renewing capacity, long-term viability, and multilineage potential to overcome these limitations. Zuk (2001) supra. There are two general categories of stem cells—embryonic and adult stem cells. While the clinical potential of embryonic stem cells is enormous, their use is highly limited due to ethical considerations and cell regulation issues. As a result, much of the tissue engineering focus on stem cells has turned to the use of autologous adult mesenchymal stem cells. Bone marrow is the most studied source of mesenchymal progenitor cells. Bone marrow stem cells have been shown to differentiate into multiple cell types in vitro and in vivo. Hauner et al. (1987) J. Clin. Endocrinol. Metabol. 64(4):832. However, their utility for tissue engineering has been limited, due in part to bone marrow harvest morbidity, low cell yields, and patient specific serum requirements.

Compositions containing adipose-derived stem cells (ADSC) have previously been used for tissue construction, but never to reconstitute tissue containing functional smooth muscle. For example, WO 00/53795 and related applications disclose adipose-derived stem cells and lattices substantially free of adipocytes and red blood cells and clonal populations of connective tissue stem cells. The cells are disclosed to be useful alone or within biologically-compatible compositions, to generate differentiated tissues and structures in vivo and in vitro. U.S. Pat. No. 6,391,297 discloses a composition of an isolated human adipose tissue-derived stromal cell that has been differentiated to exhibit at least one characteristic of an osteoblast that can be used in vivo to repair bone and treat bone diseases. This adipose-derived osteoblast-like cell can be optionally genetically modified or combined with a matrix. U.S. Pat. No. 6,426,222 discloses methods for inducing osteoblast differentiation from human extramedullary adipose tissue by incubating the adipose tissue cells in a liquid nutrient medium that must contain a glucocorticoid.

U.S. Pat. Nos. 6,153,432 and 6,429,013 and U.S. Patent Application Publication Nos. 2004/0166096A1 and 2002/011564A1 also disclose the use of ADSCs for cartilage repair.

U.S. Patent Application Publ. Nos. 2005/0076396 and 2001/0033834 as well as PCT Publication WO 01/62901 disclose isolated adipose tissue-derived stromal cells that have been induced to express at least one phenotypic characteristic of a neuronal, astroglial, hematopoietic progenitor or hepatic cell.

DISCLOSURE OF THE INVENTION

This invention provides compositions comprising an isolated or a purified adipose-derived stem cell (ADSC) or progeny of said ADSC and a suitable carrier, suitable for in vivo administration for tissue reconstruction. In one aspect, the suitable carrier is biocompatible, non-adsorbable, non-migratory and non-immunogenic. Example of such carriers include, but are not limited to, fibronogen, thrombin and a combination of fibrinogen and thrombin, the use of combinations of polylactic and glycolic acid (PLGA), and polycaprolactone (PCL). In yet a further aspect, the carrier or composition further includes growth facrtors, heparin, collagen, and/or laminin.

This invention also provides a purified or isolated population of ADSCs that can differentiate into a cell of the leiomyogenic lineage, e.g., smooth muscle or skeletal muscle. In yet another aspect, the population additionally can be differentiated into one or more of a lineage selected from the group consisting of osteogenic, adipogenic, chondrogenic, myogenic and neuronal.

This invention further provides a composition comprising a substantially homogeneous population of smooth muscle cells expanded from ADSCs. The smooth muscle cells overexpress a smooth muscle cell marker selected from the group consisting of alpha smooth muscle actin (ASMA), caldesmon, calponin, smoothelin, SM22 and smooth muscle myosin heavy chain (MHC).

Also provided is an isolated composition comprising a purified adipose-derived stem cell (ADSC) or progeny of said ADSC and an effective amount of laminin or heparin, effective to induce leiomyogenic differentiation. In one aspect, the composition further contains an effective amount of hydrocortisone, effective to induce leiomyogenic differentiation. In another, heparin is included to lead to differentiation.

The compositions disclosed herein are useful to reconstitute leiomyogenic cells in vivo and/or to tissue in a subject in need thereof.

BRIEF DESCRIPTION OF THE FIGURES

FIGS. 1A through 1H show the multi-lineage potential of PLA cells. Clonal populations from human PLA cells were expanded in vitro and subjected to lineage specific culture media. FIGS. 1A and 1E show PLA cells cultured in non-inductive growth media and immunostained for alpha-smooth muscle actin (ASMA). FIGS. 1B and 1F show PLA cells after culture in smooth muscle media, immunostained for ASMA. FIGS. 1C and 1G show PLA cells cultured in neurogenic media and immunostained for neuronal specific nuclei protein. FIGS. 1D and 1H show PLA cells cultured in osteogenic media and immunostained for alkaline phosphatate. FIGS. 1E through 1H are grey toned copies of the figures shown as FIGS. 1A through 1D, respectively.

FIG. 2A and 2D show hematoxylin and eosin staining showing post-injection PLA cells (arrows) in rat urethra. FIG. 2B and 2E show DiI fluorescent label highlighting human PLA cells (dark) within the rat urethra. FIGS. 2C and 2F show BrdU immunostaining of urethral injection site demonstrating PLA cells (grey) within the rat urethra. FIGS. 2D through 2F are grey toned copies of the figures shown as FIGS. 2A through 2C, respectively.

FIGS. 3A and 3E show positive human Alu in-situ staining (grey) of PLA injection site after 4 weeks in rat bladder. FIGS. 3B and 3F show negative Alu staining of control rat bladder 4 weeks after injection of HBSS into rat bladder. FIGS. 3C and 3G show DiI fluorescence of rat urethra 8 weeks after PLA injection. FIGS. 3D and 3H show DiI fluorescence of rat bladder 12 weeks after PLA injection showing incorporation of PLA cells into smooth muscle. FIGS. 3E through 3H are grey toned copies of the figures shown as FIGS. 3A through 3D, respectively.

MODES FOR CARRYING OUT THE INVENTION

Figures 2A, 2B, 2C:
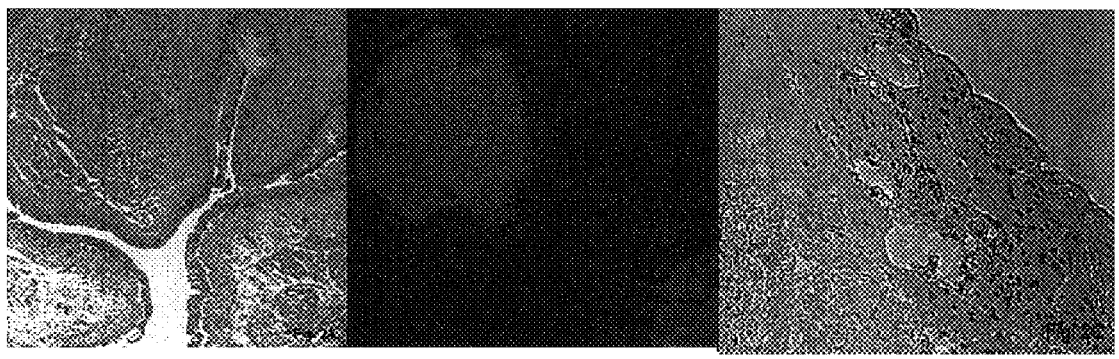
FIGS. 2A through 2F show PLA cells 2 weeks after injection into rat urethra. At two weeks post-injection, human PLA cells remained localized to the injection site.
Figures 2D, 2E, 2F:
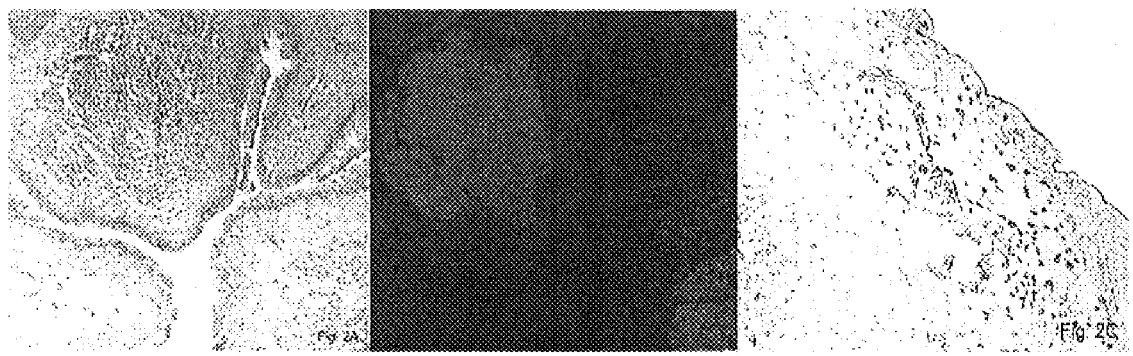
Figure 3A:
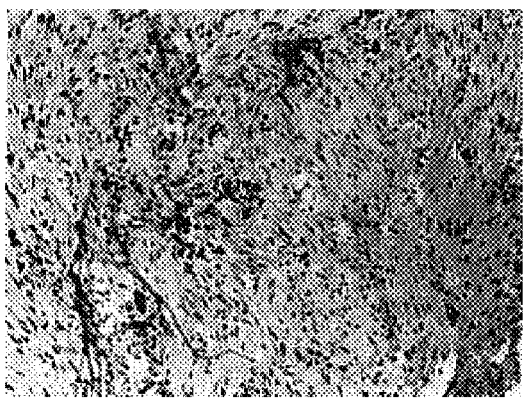
FIGS. 3A through 3H show that human PLA cells remain viable in vivo for up to 12 weeks using in vivo tracking of PLA cells using Alu and DiI labeling.
Figure 3B:
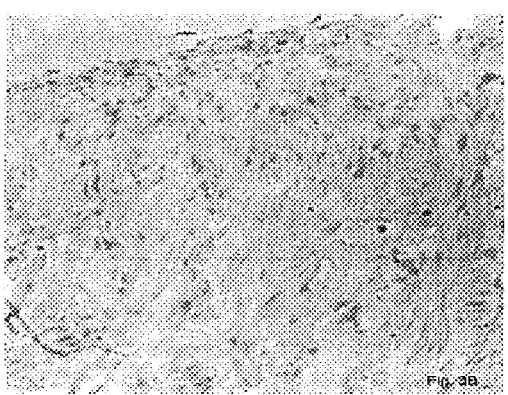
Figure 3C:
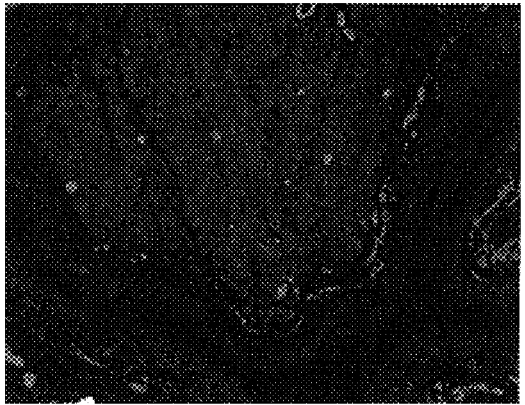
Figure 3D:
Figure 3E:
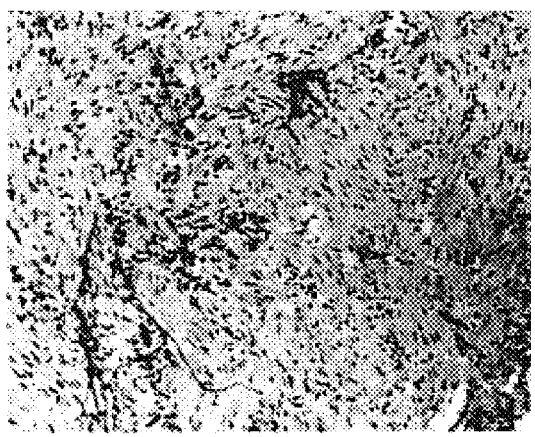
Figure 3F:
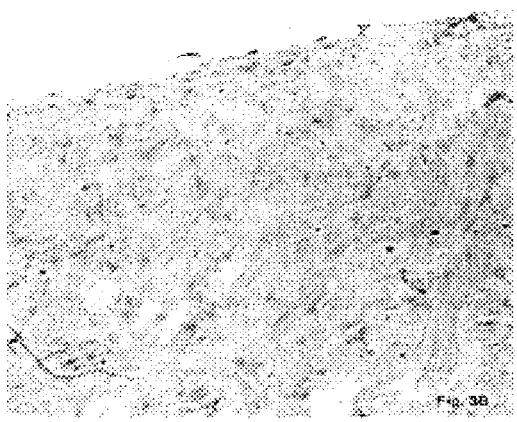
Figure 3G:
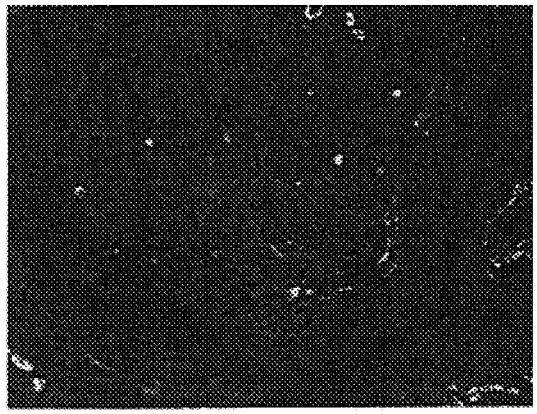
Figure 3H:
Figure 4A:
FIG. 4 (panels A and B) shows ASMA expression within PLA cells in vivo. Panel A is a color photograph and panel B is the same photograph printed in grey tone. Fluorescent staining for cell nuclei (blue), ASMA (green), and human PLA cells labeled with DiI (red) in mouse bladder wall at 8 weeks after PLA injection. Arrows indicate human PLA cells with ASMA expression (yellow).
Figure 4B:
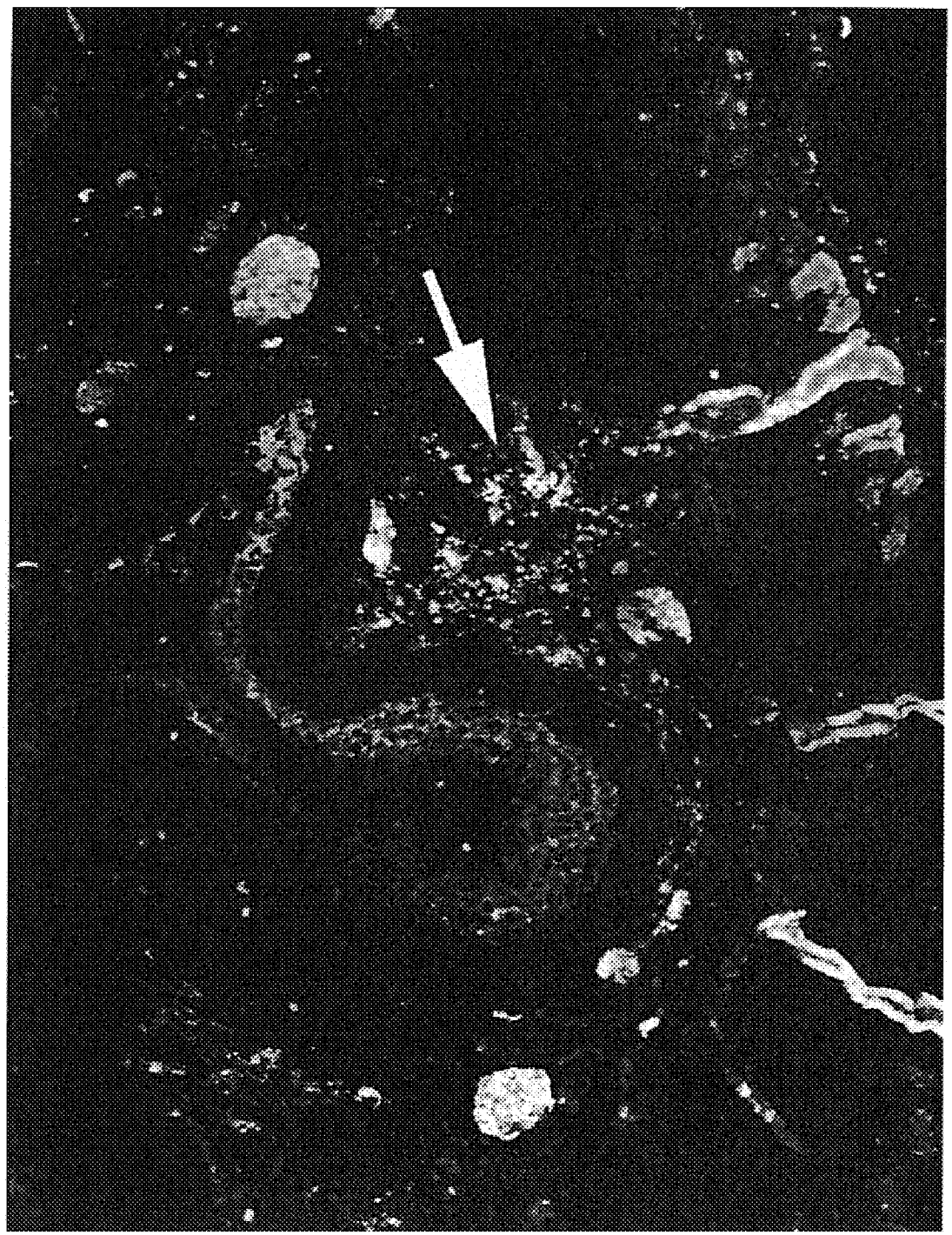

As used herein, certain terms have the following defined meanings.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a cell" includes a plurality of cells, including mixtures thereof.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

A "gene product" or alternatively a "gene expression product" refers to the amino acid (e.g., peptide or polypeptide) generated when a gene is transcribed and translated.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, "stem cell" defines an adult undifferentiated cell that can produce itself and a further differentiated progeny cell.

As used herein, the "lineage" of a cell defines the heredity of the cell, i.e. its predecessors and progeny. The lineage of a cell places the cell within a hereditary scheme of development and differentiation.

As used herein, the term "differentiates or differentiated" defines a cell that takes on a more committed ("differentiated") position within the lineage of a cell. "Dedifferentiated" defines a cell that reverts to a less committed position within the lineage of a cell.

As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurigenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

As used here, "adipose tissue" defines a diffuse organ of primary metabolic importance made up of white fat, yellow fat or brown fat. The adipose tissue has adipocytes and stroma. Adipose tissue is found throughout the body of an animal. For example, in mammals, adipose tissue is present in the omentum, bone marrow, subcutaneous space and surrounding most organs.

"Adipose-Derived Stem Cell" (ADSC) is an adult stem cell that is or has a parental cell that was obtained from a tissue source containing adipose tissue.

As used herein, the terms "treating," "treatment" and the like mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but has not yet been diagnosed as having it; (b) inhibiting a disorder, i.e., arresting its development; or (c) relieving or ameliorating the disorder, e.g., cause regression of the disorder, e.g., ADPKD.

As used herein, to "treat" includes systemic amelioration of the symptoms associated with the pathology and/or a delay in onset of symptoms. Clinical and sub-clinical evidence of "treatment" will vary with the pathology, the individual and the treatment.

As used herein and as set forth in more detail below, "conditioned medium" is medium which was cultured with a mature cell that provides cellular factors to the medium such as cytokines, growth factors, hormones, and extracellular matrix. A medium that has been exposed to mature myocytes is used to culture and induce ADSCs to differentiate into a myogenic lineage. Culturing in a medium conditioned by exposure to heart valve cells can induce differentiation into heart valve tissue. ADSCs cultured in a medium conditioned by neurons can be differentiated into a cell of the neuronal lineage. Cells cultured in medium conditioned by hepatocytes can induce differentiation into cells of the endodermal lineage.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known in the art to be capable of mediating transfer of genes to mammalian cells.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes and proteins, including enzymes.

A "primer" is a short polynucleotide, generally with a free 3'—OH group that binds to a target or "template" potentially present in a sample of interest by hybridizing with the target and, thereafter, promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer and a catalyst of polymerization, such as a DNA polymerase and, typically, a thermally-stable polymerase enzyme. Methods for PCR are well-known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

An expression "database" denotes a set of stored data that represent a collection of sequences, which in turn represent a collection of biological reference materials.

The term "cDNAs" refers to complementary DNA that is mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "expression" refers to the process by which polynucleotides are transcribed into mRNA and/or the process by which the transcribed mRNA is subsequently being translated into peptides, polypeptides or proteins. If the polynucleotide is derived from genomic DNA, expression may include splicing of the mRNA in a eukaryotic cell. "Differentially expressed" as applied to a gene, refers to the differential production of the mRNA transcribed and/or translated from the gene or the protein product encoded by the gene. A differentially expressed gene may be overexpressed or under-expressed as compared to the expression level of a normal or control cell. However, as used herein overpression is at least 1.25 fold or, alternatively, at least 1.5 fold or, alternatively, at least 2 fold expression over that detected in a normal or healthy counterpart cell or tissue. The term "differentially expressed" also refers to nucleotide sequences in a cell or tissue which are expressed where silent in a control cell or not expressed where expressed in a control cell.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels, microarrays and chips. As used herein, "solid support" also includes synthetic antigen-presenting matrices, cells and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding or in any other sequence-specific manner. The complex may comprise two strands forming a duplex structure, three or more strands forming a multi-stranded complex, a single self-hybridizing strand or any combination of these. A hybridization reaction may constitute a step in a more extensive process, such as the initiation of a PCR reaction or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90% or 95%) of "sequence identity" to another sequence, meaning that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

The antibodies can be polyclonal or monoclonal and can be isolated from any suitable biological source, e.g., murine, rat, sheep and canine.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')2 fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Nati. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The terms "monoclonal antibody" or "monoclonal antibody composition" as used herein refer to a preparation of antibody molecules of a single molecular composition. A monoclonal antibody composition displays a single binding specificity and affinity for a particular epitope.

A "human monoclonal antibody" refers to antibodies displaying a single binding specificity which have variable and constant regions derived from human gremlin immunoglobulin sequences.

By "PPAR y agonist" is meant a compound capable of activating the peroxisome proliferator-activated receptor gamma (PPAR y). Preferably the PPAR y agonist is indomethacin or any indomethacin derivative.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provisio that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

An "effective amount" is an amount sufficient to effect beneficial or desired results whether it is therapeutic or diagnostic. An effective amount can be administered in one or more administrations, applications or dosages.

Although Adipose-Derived Stem Cells (ADSCs) have been shown to differentiate into adipogenic, chrondrogenic, osteogenic, neurogenic and myogenic lineages, Zuk et al. (2001) Tissue Eng. 7:211 and Zuk et al. (2002) Mol. Biol. Cell 13:4279.; Mizuno et al. (2002) Plast. Reconstr. Surg. 109: 199; Mirozono et al. (2003) Hum. Gene Ther. 14:59; and Ashjian et al. (2003) Plast. Reconstr. Surg. 111:1922). Applicants for the first time show that ADSCs can differentiate into cells of the leiomyogenic lineage, specifically, smooth muscle cells.

ADSCs are pluripotent cells that are abundant in adipose tissue, amenable to harvesting under local anesthesia, and phenotypically similar to mesenchymal stem cells. Zuk et al. (2001) and (2002) supra. Adipose tissue, like bone marrow, is derived from the mesoderm and contains a supportive stroma of regenerative pluripotent progenitor cells and it is easily processed into a biocompatiable form called Processed Lipoaspirate or "PLA". Unlike its bone marrow counterpart, adipose tissue is easily accessible and overwhelmingly abundant. Clonal expansions of single PLA cells have demonstrated pluripotency and self-renewing capacity identical to mesenchymal stem cells.

The multipotent capacity of PLA cells, combined with their vast availability and ease of procurement, makes PLA cells an ideal source of autologous tissue for smooth muscle reconstruction. Applicants show and claim that when PLA cells are cultured in smooth muscle growth media in vitro, they differentiate into a smooth muscle phenotype. Applicants also show that when PLA cells were injected into the gerintourinary tract, smooth muscle cells incorporated in the tissue and expressed alpha smooth muscle actin (ASMA) an early marker of developing smooth muscle. ASMA also is an important protein for smooth muscle structure and contraction, and it is upregulated with smooth muscle differentiation. In addition, the Applicants have shown the differentiation of these cells into functional smooth muscle cells. The expression of markers unique to mature contractile smooth muscle cells can be induced in vitro and in vivo, including smooth muscle myosin heavy chain (MHC).

Thus, in one aspect, this invention provides a method for inducing leiomyogenic differentiation of a purifed or isolated adipose-derived stem cell (ADSC) or progeny thereof (e.g., an ADSC progenitor cell) by contacting the cell with an effective amount of a source of laminin or heparin, alone or in combination with an effective amount of hydrocortisone.

As used herein, leiomyogenic differentiation shall mean smooth muscle differentiation. In one embodiment, the cells also are contacted with an effective amount of growth factor, e.g., TGFβ-1 (purified or isolated), platelet derived growth factor, retinoic acid, interleukin 1 and ascorbic acid, all in an amount effective to induce leiomyogenic differentiation. In addition, the invention provides a system or a method to study cell function, specifically its ability to contract or relax to different pharmacologic agents.

In an alternative embodiment, the ADSCs are contacted with an effective amount of a lineage-specific differentiation factor for induction into other mesodermal or ectodermal lineages. These alternative differentiation factors are known in the art (Zuk et al. (2001) and (2002) supra; Mizuno et al. (2002) supra; Morizono et al. (2002) supra; Ashjian et al. (2003) supra; U.S. Pat. No. 6,777,231B and U.S. Patent Publ. No.2005/0076396) and exemplified below.

Suitable sources of purified or isolated ADSCs and/or progeny thereof include, but are not limited to processed lipoaspirate (PLA), a substantially homogeneous population of ADSC, a clonal population of ADSC and a single, isolated ADSC. Methods to obtain and identify these cells are known in the art and described infra.

The contacting can be conducted in vitro or in vivo. When practiced in vitro, the method provides a simple system to screen for agents such as small molecules or biomolecules that affect leiomyogenic differentiation. When practiced in vivo, the method provides a means to reconstitute smooth muscle cells and other tissue.

Commercial sources of leiomyogenic differentiation factors and growth factors are readily available. Examples of such include, but are not limited to Cascade, Sigma, Mediatech, etc. Alternatively, the differentiation and/or growth factors are provided by co-culturing the cells with a tissue source to provide the differentiation factors. The tissue source can be allogeneic or autologous to the cells.

Applicants exemplify herein that PLA-containing ADSCs when injected into the bladder or urethra remain at the site of injection, remain viable up to 12 weeks and demonstrate smooth muscle differentiation with time.

This invention also provides an isolated composition produced by each of the above-described methods. Such compositions comprise an isolated or a purified adipose-derived stem cell (ADSC) or a progeny of said ADSC and an effective amount of any one or more of laminin, heparin, collagen, or hydrocortisone wherein the effective amount induces leiomyogenic differentiation of the cell.

The compositions can alternatively contain an effective amount of growth factor. Use of the terms such as "growth factors, cytokines, hormones" is to be exemplary but not limited to the following specific factors including, TGFβ-1, growth hormone, erythropoeitin, thrombopoietin, interleukin 1, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels. Additional components are optionally added to the culture medium. Such components include but are not limited to antibiotics, albumin, amino acids, and other components known to the art for the culture of cells. Additionally, components optionally added to enhance the differentiation process. By "chemical agents" is meant steroids, retinoids, and other chemical compounds or agents that induce the differentiation of adipose derived stromal cells.

Effective amounts of the differentiation and/or growth factors can be empirically determined by those of skill in the art. It is appreciated that such amounts will vary with the source of the cells, the ultimate composition (differentiated cell type(s)) desired after culturing or the differentiation of the cells and/or growth factors and the ultimate utility for the composition. An effective amount for an in vitro screen will not necessarily be the same as when the composition is to be administered to a patient.

The growth and differentiation of the ADSCs or progeny can be monitored by morphological, immunohistochemical or molecular methods which are described infra. Culturing the cells in vitro or in vivo with an effective amount of laminin or heparin induces the cells to differentiate into smooth muscle cells. The addition of hydrocortisone to the cells induces the cells to differentiate into skeletal muscle cells. Contacting the cells with additional growth factors induces differentiation into other cell types, such as osteogenic, adipogenic, chondrogenic, myogenic and neuronal. Appropriate medium and conditions for induction into the these cell types are exemplified infra.

In addition, this application refers to a system to allow the study of contraction and relaxation of these and other smooth muscle cells. By embedding the differentiated cells in a special collagen matrix alone or in combination of other matrices and evaluating the response to electrical field stimulation and different pharmacologic agents provides a system to evaluate not only the receptors present in these cells, but more importantly a system to aid in the design of new therapeutic agents with an effect on smooth muscle cells (i.e. drugs for the cardiovascular system, drugs for pre-term labor). In an alternative embodiment, the system is composed of other materials such as PLGA, PCL and others.

Isolation, Culturing and Expansion of ADSCs

Methods to separate, isolate and expand ADSCs are known in the art and described, for example in U.S. Pat. Nos. 6,391, 2971B1; 6,777,231B1; Burris et al. (1999) Mol Endocrinol 13:410-7; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. 7(6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13: 513-517; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. Dec. 7, 2001; (6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13:513-517; Zuk et al. (2001) Tissue Eng. 7: 211-228.

ADSCs can be obtained from any animal (alive or dead) so long as adipose stromal cells within the animal are viable. Suitable tissue sources of ADSCs include, but are not limited to any fat-containing tissue, e.g., brown or white adipose tissue such as subcutaneous white adipose tissue. Typically, human adipose tissue is obtained from a living donor using surgical excision or suction lipectomy. In some embodiments, the fat tissue is obtained from a pre-selected region on the subject, i.e., inguinal, retroperitoneal and gondal, or any combination thereof. One can also pre-select for a differentiated population by isolating and using ADSCs isolated from a particular region of a donor. Applicants have discovered that cells from each of inguinal, retroperitoneal and gondal sites have multi-lineage capacity but higher osteogenic capacity was seen with cells isolated from the inguinal depot while the population isolated from the retroperitoneal site presented the greatest number of fatty cells upon differentiation.

In yet another method of isolating adipose-derived stromal cells a mechanical system such as described in U.S. Pat. No. 5,786,207 to Katz et al is used. A system is employed for introducing an adipose tissue sample into an automated device, subjecting it to a washing phase and a dissociating phase wherein the tissue is agitated and rotated such that the resulting cell suspension is collected into a centrifuge-ready receptacle. This device isolates the adipose-derived cells from the tissue while preserving the cellular integrity of the desired cells.

The separated ADSC-containing tissue can be washed with any suitable physiologically-compatible solution, such as phosphate buffer saline (PBS) prior to processing for diagnostic or therapeutic use. For example, the tissue can be rinsed with PBS, agitated and allowed to rest until the tissue settles or separates from the buffer. In one aspect, the tissue is degraded to dissociate the adipose cells or tissue from surrounding tissue, e.g., by enzyme degradation and neutralization mechanical agitation, sonic energy or thermal energy. The various methods can be combined and/or repeated as necessary.

Three layers form after settlement of the dissociated tissue. The top layer is a free lipid layer. The middle layer includes the lattice and adipocyte aggregates. The bottom layer or cell pellet after centrifugation contains the ADSCs.

The cellular fraction of the bottom layer is concentrated into a pellet by any suitable method, e.g., centrifugation, and retained for further processing. This ADSC-containing pellet previously has been referred to in the art as as the adipose-derived stem cell-enriched fraction (ADSC-EF) or stromal vascular fraction (SVF). See U.S. Patent Appl. Publ. No. 2005/0076396A1. The composition typically contains erythrocytes (RBCs) which are removed by lysing and further processing. Methods for lysis of removed RBCs are known in the art (e.g., incubation in hypotonic medium).

The pellet is resuspended and can be further washed in physiologically compatible buffer, centrifuged, and resuspended one or more successive times to achieve greater purity. The cells of the washed and resuspended pellet are ready for plating. This composition is referred to herein as Processed Lipoaspirate or "PLA".

In addition to the experimental examples described infra, paragraph [0200] of U.S. Patent App. Publ. No. 2005/0076396A1, details one appropriate protocol for the separation and isolation of ADSCs. Briefly, the authors of the patent publication stated that a hollow blunt-tipped cannulae was introduced into the subcutaneous space through small (N 1 cm) incisions of a patient undergoing elective liposurgery. The cannulae was attached to a gentle suction and moved through the adipose compartment, mechanically disrupting the fat tissue. A solution of saline and the vasoconstrictor, epinephrine, was infused into the adipose compartment to minimize blood loss and contamination of the tissue by peripheral blood cells. The raw lipoaspirate (approximately 300 cc) was processed according to established 10 methodologies in order to obtain the stromal vascular fraction (SVF). Hauner et al. (1987) J. Clin. Endocrinol. Metabol. 64: 832-835; Katz et al. (1999) Clin. Plast. Surg. 26: 587-603, viii. The authors reported that to isolate the SVF, lipoaspirates were washed extensively with equal volumes of Phosphate Buffered Saline (PBS) and the extracellular matrix (ECM) was digested at 37° C. for 30 minutes with 0.075% collagenase. Enzyme activity was neutralized with Dulbecco's Modified Eagle's Medium (DMEM), containing 10% Fetal Bovine Serum (FBS) and centrifuged at 1200×g for 10 minutes to obtain a high-density SVF pellet. The pellet was resuspended in 160 mM $NH_4Cl$ and incubated at room temperature for 10 minutes to lyse contaminating red blood cells. As reported by the authors, the SVF was collected by centrifugation, as detailed above, filtered through a 100 Nm nylon mesh to remove cellular debris and incubated overnight at 37° C./5% $CO_2$ in Control Medium (DMEM, 10% FBS, 1% antibioti-dantimycotic solution). Following incubation, the plates were washed extensively with PBS to remove residual non-adherent red blood cells to obtain PLA. The authors also reported that the cells were maintained at subconfluent levels to prevent spontaneous differentiation.

ADSCs in the PLA can be isolated to multiple single cells or a substantially homogeneous composition by methods that include, but are not limited to, cell sorting, size fractionation, granularity, density, molecularly, morphologically, and immunohistologically using methods described in the art and infra for ADSCs, as well as methods described for other stem cells with minor modifications apparent to those of skill in the art. Such methods are described for hematopoietic stem cells (Yoon et al. (2005) J. Clin. Invest. 115(2):326-338; Camargo et al. (2003) Nat. Med. 9(12):1520-1527; and Matsuzaki et al. (2004) Immunity 20:87-93), mesenchymal stem cells (WO 97/18299), and pancreatic stem cells (Suzuki et al. (2004) Diabetes 53:2143-2152).

For the purpose of illustration only, several morphological, biochemical or molecular-based methods are used to isolate the cells. In one aspect, ADSCs are isolated based on cell size and granularity since ADSCs are small and agranular. Alternatively, because stem cells tend to have longer telomeres than differentiated cells, ADSCs can be isolated by assaying the length of the telomere or by assaying for telomerase activity.

Alternatively, ADSCs can be separated from the other cells of the pellet immunohistochemically by selecting for ADSC-specific cell markers using suitable materials and methods, e.g., panning, using magnetic beads, or affinity chromatography.

In one embodiment, the stem cells are cultured without differentiation using standard cell culture media, referred to herein as control medium. (e.g., DMEM, typically supplemented with 5-15% serum (e.g., fetal bovine serum, horse serum, etc.). The stem cells can be passaged at least five times or even more than twenty times in this or similar medium without differentiating to obtain a substantially homogeneous population of ADSCs. The ADSCs can be identified by phenotypic identification. To phenotypically separate the ADSCs, the cells are plated at any suitable density which may be anywhere from between about 100 cells/$cm^2$ to about 100,000 cells/$cm^2$ (such as about 500 cells/$cm^2$ to about 50,000 cells/$cm^2$, or, more particularly, between about 1,000 cells/$cm^2$ to about 20,000 cells/$cm^2$).

Figure 5:
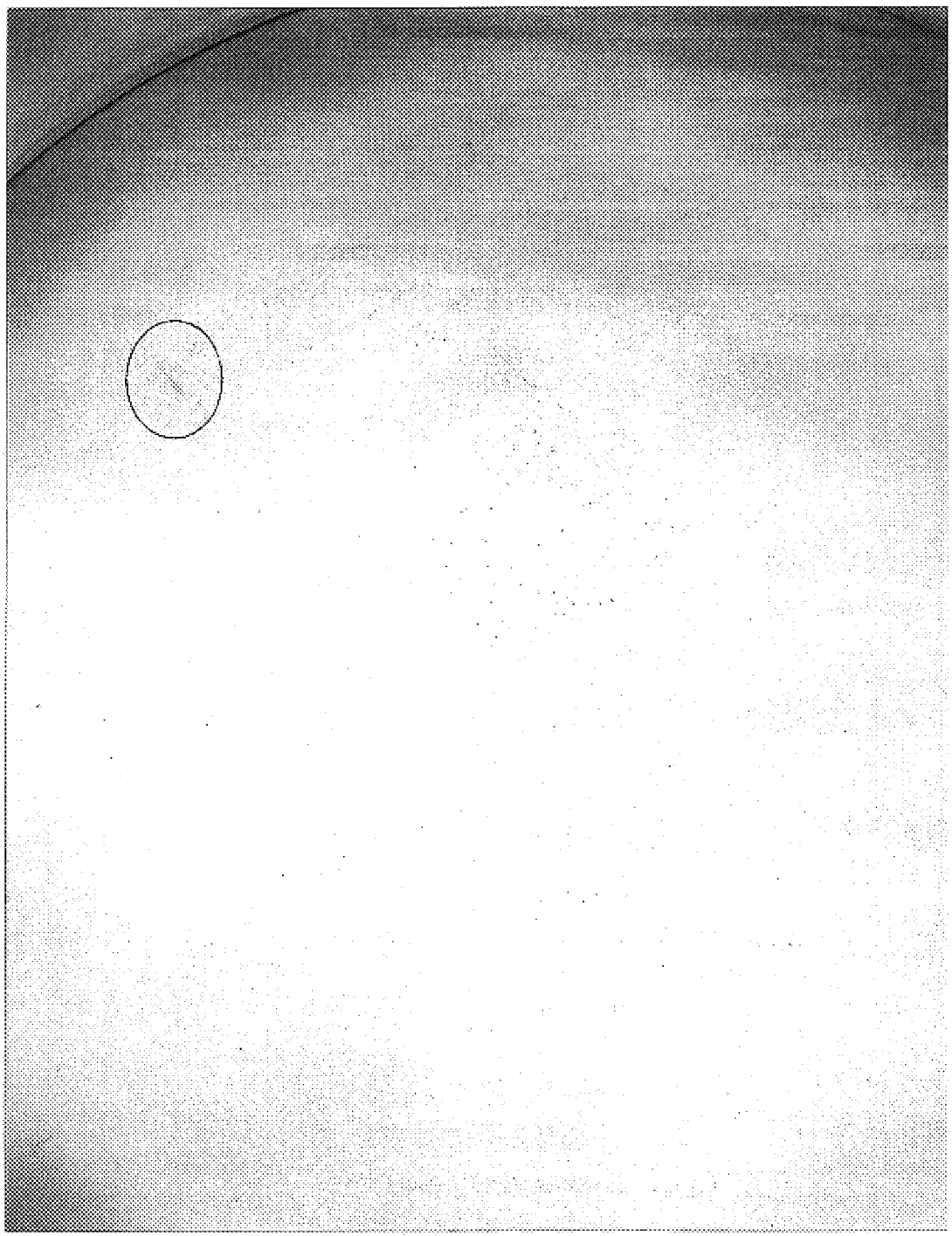
FIG. 5 shows a singe, isolated ADSC that was subsequently differentiated into the various tissue types described herein.

After passaging for several days, ADSCs initially plated at lower densities (at less than 500 cells/$cm^2$, or alternatively, less than about 300 cells/$cm^2$ or alternatively, at less than 100 cells/$cm^2$) can be used to obtain a clonal population of ADSCs by any suitable method such as by physically picking and seeding cells into separate plates (such as the well of a multi-well plate). Alternatively, the stem cells can be subcloned into a multi-well plate at a statistical ratio for facilitating placing a single cell into each well (e.g., from about 0.1 to about 1 cell/well or even about 0.25 to about 0.5 cells/well, such as 0.5 cells/well). Cloning can be facilitated by the use of cloning rings. See MacFarland, D.C. (2000) Methods in Cell Sci. 22:63-66. Alternatively, where an irradiation source is available, clones can be obtained by permitting the cells to grow into a monolayer and then shielding one and irradiating the rest of the cells within the monolayer. The surviving cell then will grow into a clonal population. Alternatively, PLA cells can be diluted to a density of 10 cells/ml and plated on Nunclon 96-well plates (Nalge Nunc International). Only wells that contain a single cell at the outset of the culture period are assayed for colony formation. Clones are detectable by microscopy after 4 to 5 days. These colonies are again diluted similarly and replated to get one cell per well (FIG. 5 shows one cell in par well). Each clone is then transferred into a single well in a 12 well or 24 well plate. The single PLA-cell cell derived colonies are expanded in cloning medium. Alternatively, single cells that can then be expanded can be isolated using a modification of the procedure described in Camargo, F.D. et al. (2003) supra.

For the purpose of illustration only, a preferred culture condition for cloning stem cells comprises about 213 $F_{12}$ medium+20% serum (preferably fetal bovine serum) and about 113 standard medium that has been conditioned with stromal cells or 15% FBS, 1% antibiotic/antimycotic in F-12/DMEM [1:1]) (e.g., cells from the stromal vascular fraction of liposuction aspirate, the relative proportions can be determined volumetrically).

In addition to the experimental example discussed infra, paragraphs [0179] and [0180] of U.S. Patent Appl. Publ. No. 2005/0076396A1 describe the cloning of ADSCs. Briefly, the authors reported that PLA cells were plated at about 5,000 cells/100 mm dish and cultured and that after some rounds of cell division, some clones were picked with a cloning ring and transferred to wells in a 48 well plate. As reported, the medium was changed twice weekly and the cells were cultured for several weeks until they were about 80% to about 90% confluent (at 37° C. in about 5% $CO_2$ in 213 $F_{12}$ medium +20% fetal bovine serum and 113 standard medium that was first conditioned by cultured PLA obtained following the protocol described in Example 1 and referred to as the "cloning medium"). Thereafter, the authors reported that each culture was transferred to a 35 mm dish and grown, and then retransferred to a 100 mm dish and grown until close to confluent. Following this, the authors report that one cell population was frozen, and the remaining populations were plated on 12 well plates, at 1000 cells/well.

In Paragraph [0180], the authors reported that cells were cultured for more than 15 passages in cloning medium and monitored for differentiation as indicated in Example 1 in the published application. The undifferentiated state of each clone remained true after successive rounds of culturing.

ADSCs, whether clonal or not, can be cultured in a specific inducing medium to induce the ADSC to differentiate and express its multipotency. The ADSCs give rise to cells of smooth muscle, mesodermal, ectodermal and endodermal lineage, and combinations thereof. Thus, one or more ADSCs derived from a multipotent ADSC can be treated to differentiate into a variety of cell types.

Phenotypic Differentiation

Smooth Muscle Differentiation: To induce leimyogenic differentiation, ADSCs can be cultured in inductive medium (Medium MCDB 131 (Sigma, MI)) supplemented with 1% FBS plus 100 U/ml heparin). Alternatively the media can be supplemented with 2% FBS and 200 U/ml heparin. When differentiated in vitro, the cells can be cultured in the presence of an effective amount of laminin, collagen, and/or heparin.

Adipogenic Differentiation: To induce adipogenic differentiation, ADSCs can be cultured in media containing a glucocorticoid (e.g., dexamethasone, hydrocortisone, cortisone, etc.), insulin, a compound which elevates intracellular levels of cAMP (e.g., dibutyryl-CAMP, 8-CPT-CAMP (8-(4)chlorophenylthio)-adenosine 3', 5' cyclic monophosphate; 8-bromo-CAMP; dioctanoyi-CAMP, forskolin etc.), and/or a compound which inhibits degradation of CAMP (e g , a phosphodiesterase inhibitor such as isobutyl methyl xanthine (IBMX), methyl isobutylxanthine, theophylline, caffeine, indomethacin, and the like), and serum. Thus, exposure of the ADSCs to between about 1 µM and about 10 µM insulin in combination with about $10^{-9}$ µM to about $10^{-6}$ M to (e.g., about 1 µM) dexamethasone can induce adipogenic differentiation. Such a medium also can include other agents, such as indomethacin (e.g., about 100 µM to about 200 µM), if desired, and preferably the medium is serum-free. Alternatively, ADSCs cultured in DMEM, 10% FIBS, 1 µM dexamthasone, 10 µM insulin, 200 µM indomethacin, 1% antibiotic/antimicotic, (ABAM), 0.5 mM IBMX, take on a adipogenic phenotype.

Osteogenic Differentiation: ADSCs cultured in a composition comprising about $10^{-7}$ M and about $10^{-9}$ M dexamethasone (e.g., about 1 Ah) in combination with about 10 µM to about 50 µM ascorbate-2-phosphate and between about 10 nM and about 50 nM β-glycerophosphate are induced to differentiate into cells of the osteogenic lineage. The medium can further include serum (e.g., bovine serum, horse serum, etc.). An alternative medium contains DMEM, 10% FBS, 5% horse serum, 50 µM hydrocortisone, $10^{-7}$ M dexamethosone, 50 µM ascorbate-2-phosphate, 1% ABAM.

Myogenic Differention: ADSCs cultured in a composition comprising between about 10 µM and about 100 µM hydrocortisone, preferably in a serum-rich medium (e.g., containing between about 10% and about 20% serum (either bovine, horse, or a mixture thereof)) will differentiate into cells of the myogenic lineage. Other glucocorticoids that can be used include, but are not limited to, dexamethasone. Alternatively, 5'-azacytidine can be used instead of a glucocorticoid. Alternatively, ADSCs cultured in DMEM, 10% FIBS, $10^{-7}$M dexamethosone, 50 nM ascorbate-2-phosphate, 10 mM beta-glycerophosphate, 1% ABAM, take on a myogenic phenotype.

Chrondrogenic Differentiation: To induce chondrogenic differentiation, cells can be cultured in a composition comprising between about 1 µM to about 10 µM insulin and between about 1 µM to about 10 µM transferrin, between about 1 ng/ml and 10 ng/ml transforming growth factor (TGF) β 1, and between about 10 nM and about 50 nM ascorbate-2-phosphate (50 nM). For chondrogenic differentiation, preferably the cells can be cultured in high density (e.g., at about several million cells/ml or using micromass culture techniques), and also in the presence of low amounts of serum (e.g., from about 1% to about 5%).

Fibrogenic Differentiation: ADSCs cultured in DMEM, 50~Mascorbate-2-phosphate, 6.25 pg/ml transferin, 10 ng/ml insulin growth factor (IGF-1), 5 ng/ml TGFβ-1, 5 ng/ml basic fibroblast growth factor (bFGF; used only for one week), are induced to differentiate into cells of the chondrogenic phenotype.

Ectodermal Differentiation: To induce ectodermal (e.g., neurogenic) differentiation, ADSCs can be cultured in a medium comprising DMEM, no serum and 5-10 mM . β-mercaptoethanol and assume an ectodermal lineage.

Dedifferentiation: Can be induced to dedifferentiate into a developmentally more immature phenotype (e.g., a fetal or embryonic phenotype) by co-culturing the cells with cells isolated from fetuses or embryos, or in the presence of fetal serum.

In addition to above cuture conditions, ADSCs co-cultured with mature or immature cells of a respective germ layer can be induced to differentiate into a mesodermal, ectodermal, or endodermal lineage. For example, co-culturing with differentiated mature cells includes, but is not limited to, myogenic differentiation induced by co-culturing the ADSCs with myocytes or myocyte precursors; induction of the ADSCs into a neural lineage by co-culturing with neurons or neuronal precursors, and induction of the ADSCs into an endodermal lineage, can occur by co-culturing with mature or precursor pancreatic cells or mature hepatocytes or their respective precursors.

For co-culture, ADSCs can be co-cultured under conditions wherein the ADSC is in contact or close proximity to the non-ADSC. This can be achieved, for example, by seeding the cells as a heterogeneous population of cells onto a suitable culture substrate. Alternatively, the ADSCs can first be grown to confluence to serve as a substrate for the non-ADSCs within the conditioned medium.

This disclosure shows smooth muscle differentiation of ADSCs and PLA cells by co-culturing them with bladder or other organ smooth muscle cells. In one embodiment, rat bladder smooth muscle cells and human ADSCs were trypsinized and resuspended in DMEM at 1:1 or 5:1 ratio. FACS analysis was performed using specific antibodies against HLA-ABC, a surface marker for human cells, and smooth muscle markers actin, calponin, caldesmon, and myosin heavy chain. After two weeks of co-culturing, 16% of human ADSC's expressed smooth muscle markers.

Characterization of Cultured ADSC or Progeny

Methods to characterize differentiated cells that develop from the ADSCs, include, but are not limited to, histological, morphological, biochemical and immunohistochemical methods, or using cell surface markers, or genetically or molecularly, or by identifying factors secreted by the differentiated cell, and by the inductive qualities of the differentiated ADSCs. Molecular characterization of differentiated ADSCs can be achieved by measurement of telomere length since undifferentiated stem cells have longer telomeres than differentiated cells. Alternatively or in addition, the cells can be assayed for the level of telomerase activity.

Molecular Markers and Methods: For the purpose of illustration only, mesodermal lineage markers include, but are not limited to, MyoD, myosin, α-actin, brachyury, xFOG, Xtbx5 FoxF1, XNkx-2.5. Ectodermal lineage molecular markers include but are not limited to N-CAM, GABA and epidermis specific keratin. Molecular markers that characterize cells of the endodermal lineage include, but are not limited to, Xhbox8, Endo1, Xhex, Xcad2, Edd, EF1-α, HNF3-β, LFABP, albumin, insulin. Unless otherwise stated, mammalian homologs of the markers can be used.

Detection of molecular markers can be by any appropriate method, including for example, detecting the quantity of mRNA transcribed from the marker gene or the quantity of cDNA produced from the reverse transcription of the mRNA transcribed from the gene or the quantity of the polypeptide or protein encoded by the gene. These methods can be performed on a sample by sample basis or modified for high throughput analysis. Additionally, databases containing quantitative full or partial transcripts or protein sequences isolated from a cell sample can be searched and analyzed for the presence and amount of transcript or expressed gene product.

In assaying for an alteration in mRNA level, nucleic acid contained in a sample of cells is first extracted according to standard methods in the art. For instance, mRNA can be isolated using various lytic enzymes or chemical solutions according to the procedures known in the art or extracted by nucleic-acid-binding resins following the accompanying instructions provided by manufactures. The mRNA of a gene contained in the extracted nucleic acid sample is then detected by hybridization (e.g., Northern blot analysis) and/or amplification procedures according to methods widely known in the art.

In certain embodiments, it will be advantageous to employ nucleic acid probe or primer sequences in combination with an appropriate means, such as a label, for detecting hybridization and therefore complementary sequences. A wide variety of appropriate indicator means are known in the art, including fluorescent, radioactive, enzymatic or other ligands, such as avidin/biotin, which are capable of giving a detectable signal. One can employ a fluorescent label or an enzyme tag, such as urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

Hybridization reactions can be performed under conditions of different "stringency". Relevant conditions include temperature, ionic strength, time of incubation, the presence of additional solutes in the reaction mixture such as formamide and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. Sambrook et al. (1989) supra.

Amplification using the polymerase chain reaction and primers can also be utilized to detect the presence or absence of genes or gene transcripts that are differentially expressed in various phenotypic lineages. For the purpose of this invention, "amplification" means any method employing a primer-dependent polymerase capable of replicating a target sequence with reasonable fidelity. Amplification may be carried out by natural or recombinant DNA-polymerases such as T7 DNA polymerase, Klenow fragment of E.coli DNA polymerase and reverse transcriptase.

A known amplification method is PCR, MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, $Mg^{2+}$ ATP concentration, pH and the relative concentration of primers, templates and deoxyribonucleotides.

After amplification, the resulting DNA fragments can be detected by agarose gel electrophoresis followed by visualization with ethidium bromide staining and ultraviolet illumination. A specific amplification of differentially expressed genes of interest can be verified by demonstrating that the amplified DNA fragment has the predicted size, exhibits the predicated restriction digestion pattern and/or hybridizes to the correct cloned DNA sequence.

The probes also can be attached to a solid support for use in high throughput screening assays using methods known in the art. PCT WO 97/10365 and U.S. Pat. Nos. 5,405,783; 5,412,087 and 5,445,934; for example, disclose the construction of high density oligonucleotide chips which can contain one or more of the sequences disclosed herein. Using the methods disclosed in U.S. Pat. Nos. 5,405,783; 5,412,087 and 5,445,934; the probes of this invention are synthesized on a derivatized glass surface. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

The expression level of a gene can also be determined through exposure of a nucleic acid sample to a probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device, such as a confocal microscope. See, U.S. Pat. Nos. 5,578,832 and 5,631,734. The obtained measurement is directly correlated with gene expression level.

The probes and high density oligonucleotide probe arrays also provide an effective means of monitoring expression of the gene of interest. They are also useful to screen for compositions that upregulate or downregulate the expression of the gene of interest which can be a useful marker of de-differentiation.

In one embodiment, the hybridized nucleic acids are detected by detecting one or more labels attached to the sample nucleic acids. The labels may be incorporated by any of a number of means known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g., fluorescein-labeled UTP and/or CTP) incorporates a label into the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein and the like), radiolabels (e.g., $^3$H, $^{125}$I, $^{35}$S, $^{14}$C or $^{32}$P) enzymes (e.g., horseradish peroxidase, alkaline phosphatase and others commonly used in an ELISA) and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate and colorimetric labels are detected by simply visualizing the colored label. For a detailed review of methods of labeling nucleic acids and detecting labeled hybridized nucleic acids. LABORATORY TECHNIQUES IN BIOCHEMISTRY AND MOLECULAR BIOLOGY, Vol. 24: Hybridization with Nucleic Acid Probes, P. Tijssen, ed. Elsevier, N.Y. (1993).

Results from the chip assay are typically analyzed using a computer software program. See, for example, EP 0717 113 A2 and WO 95/20681. The hybridization data is read into the program, which calculates the expression level of the targeted gene(s).

Immunhistochemical Characterization

Alternatively, cellular differentiation can be determined using immunohistochemical techniques or histologically, using tissue-specific antibodies or stains. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), Western blot analysis, immunoprecipitation assays, immunofluorescent assays and PAGE-SIDS.

For example, to assess adipogenic differentiation, the differentiated ADSCs can be stained with fat-specific stains (e.g., Oil Red O, Safarin Red, Sudan Black, etc.) or with labeled antibodies or molecular markers that identify adipose-related factors (e.g., PPAR-y, adipsin, lipoprotein lipase, etc.).

Osteogenesis can be assessed by staining the differentiated ADSCs with bone-specific stains (e.g., alkaline phosphatase, von Kossa, etc.) or with labeled antibodies or molecular markers that identify bone-specific markers (e.g., osteocalcin, osteonectin, osteopontin, type I collagen, bone morphogenic proteins).

Myogensis can be assessed by identifying classical morphologic changes (e.g., polynucleated cells, syncitia formation, etc.), or assessed biochemically for the presence of muscle-specific factors (e.g., myo D, myosin heavy chain, etc.).

Chondrogenesis can be determined by staining the cells using cartilage-specific stains (e.g., Alcian blue) or with labeled antibodies or molecular markers that identify cartilage-specific molecules (e.g., sulfated glycosaminoglycans and proteoglycans, keratin, chondroitin, Type II collagen, etc.) in the medium.

Screening Assays

This invention also provides a screen to assess candidate drugs and therapies that effect smooth muscle function and differentiation. The screen comprises contacting a composition identified above (containing ADSCs) with an amount of a candidate drug or agent and comparing the growth and/or differentiation of the cells by methods known in the art against a control composition that did not receive the therapy. In addition or alternatively, the candidate screen can be compared against a known drug or therapy that has a known therapeutic effect, e.g. beta-blockers such as carbachol, commercially available as Carbastet in the U.S and Canada.

This invention also provides a screen to quantitate smooth muscle function and to quantitate the effect of factors, agents or culture conditions on smooth muscle function. This invention provides an in vitro method to assay for modulation of smooth muscle contractile response comprising growing a substantially homogeneous population of expanded smooth muscle cells in a suitable carrier and adding a test agent to the smooth muscle cell population and monitoring the effect of the drug on smooth muscle contraction. In one aspect, the suitable carrier is a polymer gel and the test agent is any drug, pharmaceutical or agent that is believed to effect smooth muscle contraction.

As is apparent to one of skill in the art, the method can be modified for high throughput analysis and suitable cells may be cultured in microtiter plates and several agents may be assayed at the same time by noting changes in the timing and degree of smooth muscle contraction.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides and synthetic organic compounds based on various core structures; these compounds are also included in the term "agent". In addition, various natural sources can provide compounds for screening, such as plant or animal extracts and the like. It should be understood, although not always explicitly stated that the agent is used alone or in combination with another agent, having the same or different biological activity as the agents identified by the inventive screen. The agents and methods also are intended to be combined with other therapies.

When the agent is a nucleic acid, it can be added to the cell cultures by methods known in the art, which includes, but is not limited to calcium phosphate precipitation, microinjection or electroporation. Alternatively or additionally, the nucleic acid can be incorporated into an expression or insertion vector for incorporation into the cells. Vectors that contain both a promoter and a cloning site into which a polynucleotide can be operatively linked are well known in the art and briefly described infra.

When the agent is a composition other than a DNA or RNA nucleic acid molecule, the suitable conditions comprise directly added to the cell culture or added to culture medium for addition. As is apparent to those skilled in the art, an "effective" amount must be added which can be empirically determined.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. This assay is easily modified for high through-put.

RNA can be obtained by first inserting a DNA polynucleotide into a suitable host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook et al. (1989) supra. For instance, mRNA can be isolated using various lytic enzymes or chemical solutions according to the procedures set forth in Sambrook, et al. (1989) supra or extracted by nucleic-acid-binding resins following the accompanying instructions provided by manufactures.

Antisense nucleic acids are DNA or RNA molecules that are complementary to at least a portion of a specific transcript RNA molecule. In the cell, the antisense nucleic acids hybridize to the corresponding transcript RNA, forming a double-stranded molecule thereby interfering with the translation of the mRNA, since the cell will not translate a mRNA that is double-stranded. Antisense oligomers of about 15 nucleotides are preferred, since they are easily synthesized and are less likely to cause problems than larger molecules. The use of antisense methods to inhibit the in vitro translation of genes is known in the art. Marcus-Sakura (1988) Anal. Biochem. 172:289 and De Mesmaeker, et al. (1995) Curr. Opin. Struct. Biol. 5:343-355. The information disclosed in these publications and known to those of skill in the art, in combination with Applicants' specification, enables one of skill in the art to make and use antisense DNA or RNA molecules as therapeutic agents.

Use of an oligonucleotide to stall transcription is known as the triplex strategy since the oligomer winds around double-helical DNA, forming a three-strand helix. Triplex compounds are designed to recognize a unique site on a chosen gene. Maher, et al. (1991) Antisense Res. and Dev. 1(3):227; Helene, C. (1991) Anticancer Drug Design 6(6):569.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. A major advantage of this approach is that, because they are sequence-specific, only mRNAs with particular sequences are inactivated.

In yet another aspect, the composition is administered to one or more animals or subjects (see for example, Experiment No. 1 and 5, infra) and then the candidate drug or therapy is administered to the subject. The effect, if any, of the candidate drug on the growth and/or differentiation of the cells in the subject are compared to one or more subjects who have received an ADSC composition, but no drug. Alternatively or in addition, a composition is administered to a subject who receives a drug or therapy with a known effect that will serve as a positive control. The effect of the candidate drug or therapy can be compared to the positive control.

Reconstruction of Smooth Muscle in Vivo

This invention also provides purified adipose-derived stem cell (ADSC) or progeny of said ADSC and a biocompatible, non-adsorbable, non-migratory and non-immunogenic carrier such as a fibrin glue. Additional examples, include, but are not limited to PLGA microspheres, PCL, PLGA, carrier or peptides.

The purified ADSCs can be obtained from any suitable source, as described above. The compositions can be cultured prior to in vivo administration or they can be administered without additional expansion or differentiation (P0).

For the purpose of illustration only, examples of suitable carriers are fibrinogen, thrombin or a combination of fibrinogen and thrombin. The ratio of fibrinogen to thrombin can vary, from about 0.5:1.0 (fibrinogen:thrombin) to about 1.0: 10.0 and all variations in between. Additionally, the ratio of thrombin to $CaCl_2$ in the mixture can vary from about 1:1 to about 1:9, and all variations in between. The components can be combined prior to administration in vivo or administered as separate components and combined in vivo. Alternatively, carrier using polymers such as different combinations of polylactic and glycolic acid (PLGA) can be used. One such combination of 85% polylactic and 15% glycolic acid (or any other suitable combination) can be made into microspheres using oil-water emulsion and solvent extraction-evaporation techniques (Cohen S, et al. (1991) Pharm Res 8:713). The microspheres can then be filtered to any indicated size. For the purpose of illustration only, $1 \times 10^6$ microspheres measuring 20-50 μm can be injected alone or in combination with ADSCs. Other compounds such as polycaprolactone (PCL) or peptides can be used as injection carriers. Growth factors, angiogenic factors, neurotropic factors and factors of cell differentiation including smooth muscle cell differentiation, can be added to these injectable carriers in addition to the ADSCs. The time release of these added substances can be controlled and act on the ADSC to induce their differentiation and modulate their function. In addition, pharmacologic agents can also be incorporated.

When administered to subjects under suitable conditions, the compositions described herein are useful to reconstitute leiomyogenic cells in vivo or to reconstitute tissue containing leiomyogenic cells (such as the urinary tract, epithelial pathway or bladder). The compositions and methods are useful to treat disorders that affect smooth muscle function, e.g., urinary incontinence and bladder disease. Additional disorders include, but are not limited to vascular disorders, intestinal disorders, vesicoureteral reflux, or other disorders of smooth muscle function. The compositions can further contain an additional pharmaceutical or agent, or alternatively a polynucleotide that encodes for a therapeutic agent or for an inhibiting nucleic acid. Examples of nuclear acids include, a ribozyme, an antisense oligonucleotide, a double stranded RNA, a double-stranded interfering RNA (iRNA), a triplex RNA, an RNA aptamer, and at least a portion of an antibody molecule that binds to the gene product and inhibits its activity. Thus, in one aspect, the invention provides a method for alleviating the symptoms of bladder disease and/or urinary incontinence by delivering to a subject in need thereof an effective amount of a composition of described herein. An effective amount of the composition is applied to the area or tissue requiring therapy, e.g., bladder. In addition, for total tissue substitution, three dimensional scaffolds using similar material can be designed using PLGA, PCL, or other materials. These scaffolds can be seeded with ADSCs or smooth muscle differentiated ADSCs or PCL cells and tissues reconstructed. The inventors have demonstrated successful bladder regeneration using such scaffolds and ADSC in an animal model. These three dimensional scaffolds can be similarly coated with growth factors, differentiation factors, pharmacologic agents, and chemical agents as are known to those skilled in the art and as described herein.

Compositions and cells described herein can be further combined with a carrier, a pharmaceutically acceptable carrier or medical device which is suitable for use in diagnostic or therapeutic methods. The carrier can be a liquid phase carrier or solid phase carrier, e.g., bead, gel or carrier molecule such as a liposome. The composition can optionally further comprise at least one further compound, protein or composition.

An additional example of "carriers" includes therapeutically active agents such as biomatrices such as a fibrin glue containing at least fibrinogen and thrombin.

The cells also can be transduced with a transgene that will be expressed after administration of the composition to the subject.

EXPERIMENTAL METHODS

The following experiments are intended to illustrate, not limit the inventions as disclosed herein.

Experiment No. 1—An Animal Model

This experiment describes the development of a therapeutically-relevant animal model for the study of urinary incontinence.

All animals were handled in accordance with guidelines of the Chancellor's Animal Research Committee of the Office for Protection of Research Subjects at our institution.

A total of 140 female Sprague-Dawley retired breeder rats age 6 to 9 months weighing from 340 to 400 gm were used in this study (Charles River, Wilmington, Mass.). All animals underwent urodynamic and urethral resistance evaluation preoperatively. They were then divided into five groups and urodynamics performed at 1, 4, 8, 12 or 24 weeks postoperatively. Three affected animals were sacrificed at each time point and the bladder and urethral tissues were examined by histology and immunohistochemistry. A group of animals (n=10) underwent sham surgery where the abdominal cavity was opened and the bladder manipulated with forceps but the urethra and bladder neck were untouched. These animals were evaluated one week postoperatively. In addition, in order to evaluate the impact of parity on the development of incontinence in this animal model, 10 female virgin rats 6 months of age and weighing from 270-320 gm were used to evaluate the differences between virgin rats and retired breeders.

Cystometrogram (CMG) and Measurement of Abdominal Leak Point Pressure (ALPP): All animals were anesthetized with an intraperitoneal injection of Ketamine (70-90 mg/Kg body weight). The urinary bladder was emptied with a 22G transurethral catheter. A 2F microtip transurethral Intracath was used for bladder filling and recording via a 3-way stopcock. The tubing was connected to a pressure transducer (Duet® Logic, Medtronic, Denmark) in line with an infusion pump (Harvard Apparatus, Holliston, Mass., USA). Saline at 37° C. was infused at the rate of 100 µl per minute. A computer with data acquisition software was used for recording the cystometric studies. The infusion volume was defined as maximal bladder capacity when the first urine drop appeared at the urethral meatus in conjunction with a rapid rise of the intravesical pressure. Bladder capacity was determined as the average between three voiding cycles. The bladder was then emptied with a 22G transurethral catheter and filled to half capacity with saline mixed with methylene blue to facilitate determination of urine leakage. The transurethral catheter was then removed and a 3F Fogarty tube with 0.15 ml balloon (120403F Edwards Lifesciences, Germany) was put in the rectum and connected to the pressure transducer in order to record intra-abdominal pressures. Steady suprapubic pressure was applied manually. The pressure was increased at 10 cm $H_2O$ intervals and recorded. The lowest intra-abdominal pressure that led to leakage of urine at the urethral meatus was chosen as the ALPP. ALPP determination was determined four times for each animal. Average ALPP was reported.

Retrograde Urethral Perfusion Pressure: The retrograde urethral perfusion pressure (RUPP) estimates urethral resistance by measuring variations of intraurethral pressure to a constant flow. After completion of the ALPP determination, the bladder was emptied. The urethral meatus was catheterized with one 2F microtip transurethral Intracath and another customized 2F silicon infusion tube (SIL-C20 Instech Solomon, Pa., USA). These catheters were placed just inside the urethral meatus and therefore their tips were within the distal urethra. They were made watertight using a 5-0 polyglactin (Vicryl) suture to close the urethral meatus around the catheters. The perfusion pump was zeroed, connected to the silicon tubing and saline was then infused at a rate of 100 µl per minute. The transurethral Intracath was connected to a pressure transducer for recording. By infusing at a constant flow and measuring the pressure of the occluded urethra during early filling, urethral resistance to flow was estimated. This measurement is done early in filling, before cystometric capacity is reached or increases in bladder pressures are seen. Thus the retrograde urethral perfusion pressure (RUPP) is the pressure required to achieve and maintain an open urethral sphincter. Three measurements of RUPP were taken at each time point for each animal. The average of these measurements was reported.

Inter-Observer and Intra-Observer Variability: To determine inter-observer variability, an analysis was performed on the RUPP of 25 normal rats obtained by three independent investigators. Three animals were tested in quadruplicate to analyze intra-observer variability. Each quadruplicate study was performed under the same anesthetic. For each of the studies, the catheters were removed and the bladder was emptied between individual data point acquisitions.

Transabdominal Urethrolysis: One week after the baseline urodynamics evaluation, the animals were anesthetized with an intraperitoneal injection of Ketamine (60 mg/kg body weight (BW)) and Xylazine (5 mg/kg BW). They were placed supine on a water circulating heating pad. The abdomen was prepped and draped in standard surgical fashion. A lower abdominal midline incision was made and the bladder and urethra were identified. The proximal and distal urethra was detached circumferentially by incising the endopelvic fascia and detaching the urethra from the anterior vaginal wall and pubic bone by sharp dissection. Care was taken not to injure the ureters or compromise the inferior vesical vasculature. A cotton swab was put into the vagina in order to aid with the dissection. The rectus fascia and skin were closed with 4-0 polyglactin (Vicryl) and 4-0 Nylon sutures respectively. The animals were kept under watchful observation in a water circulating heating pad and turned from side to side until they were able to maintain sternal recumbency prior to being returned to the vivarium.

Incontinence Measurement: Measurable clinically relevant change in urethral competency was measured as ALPP or RUPP values less than one standard deviation from the preoperative mean. Results were obtained up to 6 months post-operation, shown in Table 1, below.

Histological Studies: Animals were sacrificed with overdose intravenous sodium pentobarbital (100 mg/kg BW). The whole bladder and urethra were harvested by removing the symphysis pubis and thus preserving the entire urethral segment. The specimens were fixed in 10% neutral buffered formalin overnight and embedded in paraffin. Paraffin blocks were cut in 5 μm thick sections. These were deparaffinized and hydrated with distilled water. Two sequential sections were then stained with Masson's trichrome to determine the distribution of smooth muscle and extracellular matrix.

Apoptosis: The terminal deoxynucleotidyltransferase-mediated deoxyuridine triphosphate nick-end labeling (TUNEL) assay was followed by tetramethylrhodamine deoxyuridine 5'-triphosphate (TMR) staining. An in situ cell death assay with the TMR red detection kit (Roche Diagnostic, Indianapolis, Ind.) was performed on paraffin-embedded blocks according to the manufacturer's instructions. Each slide contained a saggital section of the whole bladder and three cross sections of the urethra (one proximal, one mid and one distal urethra). Two sequential histological sections from each sacrificed animal were used. Deparaffinized tissue sections were incubated in 20 μg/ml proteinase K for 15 minutes at room temperature and incubated in TUNEL reaction mixture for 60 minutes at 37° C. in the dark. After washing in phosphate-buffered saline, the samples were counterstained with 4', 6-diamidino-2-phenylindole (DAPI, Vector Laboratory, Burlingame, Calif.). Positive controls were treated for 10 minutes with 0.5 mg/ml deoxyribonuclease I in sodium cacodylate buffer (PH 7.2). Terminal deoxynucleotidyl transferase was omitted from the nucleotide mixture for the negative controls.

Nerve Staining with Anti-Protein Gene Product 9.5 Antibody PGP 9.5: Protein gene product 9.5 (PGP9.5) is an ubiquitin hydrolase widely expressed in neuronal tissues at all stages of neuronal differentiation. For evaluation of changes in neuronal mass, PGP9.5 immunoreactivity was used as a neural marker. Two sequential sections from each sacrificed animal were deparaffinized, hydrated in distilled water and washed with phosphate-buffered saline (PBS) (Sigma, St. Louis, Mo.) at room temperature (3 times×10 min). The sections were then incubated for 1 hour at room temperature with PBS containing 2% (w/v) bovine serum albumin (BSA) (Sigma, St. Louis, Mo.) and 0.3% (v/v) Triton X-100 (Sigma, St. Louis, Mo.) in order to block nonspecific antibody binding, and then incubated with rabbit polyclonal anti-PGP9.5 neuronal marker (DAKO, Carpinteria, Calif.) at 1:500 and 4° C. overnight. The sections were labeled with a fluorescein isothiocyanate-conjugated anti-rabbit secondary antibody (Vector Laboratory, Burlingame, Calif.).

Quantitative Image Analysis: The quantitation of the staining obtained by either histochemical or immunohisto/cytochemical techniques was performed by computerized densitometry using the ImagePro 4.01 program (Media Cybernetics, Silver Spring, Md.) coupled to an Olympus BHS microscope equipped with a Spot RT digital camera.

Statistical Analysis: Data were summarized as mean ± standard deviation. Analysis was performed using statistical software (SPSS 11.0, SPSS Inc., Chicago, Ill.). Normally distributed variables were compared with the Student t test. The Kruskal-Wallis test was used for nonparametric independent multiple group comparisons and applied to test for differences in preoperative and postoperative ALPP and RUPP at each time point. Chi-square analysis was performed to test for differences in continence status before and after urethral detachment at each time point. One way ANOVA was used for multiple group comparison to test for differences in preoperative and postoperative bladder capacity and threshold pressure at each time point, as well as determination of interobserver variability. Pearson correlation coefficient was applied to the study of the correlation between ALPP and RUR. Statistical significance was determined at p values less than 0.05.

Urodynamic Evaluation: The overall changes in urodynamic parameters are shown in Table 1, below. Anatomic urethral detachment had no effect on bladder capacity, bladder filling pressures, or compliance. In addition, there were no significant changes between the baseline values of the preoperated normal rats and the sham operated animals (bladder capacity 1.6 vs. 1.4, threshold pressure 26.3 vs. 25.8, p>0.05). Statistically significant decreases were seen in ALPP and RUPP after urethrolysis at all time points (Table 1). Normal retired breeders female rats had an average baseline RUPP of 22.6 cm $H_2O$ and ALPP of 19.4 cm $H_2O$ preoperatively. There was no statistically significant difference between the baseline values of the retired breeders female rats and the sham operated animals (mean RUPP 21.9 cm $H_2O$, p>0.05; mean ALPP 21.4 cm $H_2O$, p>0.05). One week after urethrolysis, the mean ALPP and RUPP decreased to 9.8 cm $H_2O$ and 11.2 cm $H_2O$ respectively. A measurable clinically relevant change as values less than one standard deviation was considered from the preoperative mean. This change was defined as the incontinence threshold. With this definition, one week following urethrolysis, 100% and 93% of all animals had lower VLPP and RUPP than the defined incontinence threshold. These decreases in ALPP and RUPP were maintained in 75% and 69% of animals respectively for up to 24 weeks post-operatively. The Pearson correlation coefficient (r) between the individual ALPP and RUPP in all animals was 0.54 (p<0.01). On cystometry, there was evidence of very low detrusor contractions of 3-4 cm $H_2O$ not leading to leakage in approximately 10-15% of animals after 12 weeks with the majority of these presenting at 24 weeks postoperatively. No animal suffered from urinary retention or urinary obstruction.

TABLE 1

UroDynamic Evaluation
Urodynamic Assessment in an Animal Model of ISD

| | Normal Animals | ISD 1 wk. | ISD 1 mo. | ISD 2 mo. | ISD 3 mo. | ISD 6 mo. |
|---|---|---|---|---|---|---|
| Leak Point Pressure (ALPP) (cm $H_2O$) | 19 | 9 | 13 | 12 | 14 | 11 |
| Urethral Resistance (RUPP) (cm $H_2O$) | 22 | 11 | 12 | 14 | 14 | 12 |
| Animals "Incontinent" | 10% | 100% | 75% | 80% | 63% | 76% |

Analysis of the inter-observer variability of three independent investigators showed no significant variation in RUPP determination. The average variation from the mean was 8.2%. The average (± S.D.) RUPP for each investigator was 21.9 (±5.3), 25.2 (±6.8), and 19.9 (±6.1) cm $H_2O$ respectively (p=0.15). In addition, there was minimal variability within intra-observer RUPP results with an average RUPP of 21.4 cm $H_2O$ and an average standard error of the mean (SEM) of 1.1 cm $H_2O$ (range 0.7 to 1.4). In order to evaluate the effect of parity on the SUI model, ten virgin rats were evaluated for comparison. There were no significant differences in bladder capacity, threshold pressure, ALPP, or urethral resistance between retired breeder and virgin rats.

Urethral Smooth Muscle Distribution: Masson's trichrome staining revealed marked smooth muscle atrophy in the urethral wall musculature. The urethral smooth muscle to collagen ratio was 1.2:1 preoperatively. This was not significantly different from the sham-operated group (normalized preoperative ratio of 1 vs. sham ratio of 0.97, p>0.05). Following urethrolysis, the smooth muscle content of the urethra decreased by an average of 65% at 1, 4, and 8 weeks. Some recovery of the urethral smooth muscle was noted by 12 weeks post urethrolysis, however the ratio still remained below baseline (p<0.05). There was a strong correlation between RUPP and urethral smooth muscle atrophy (r=0.97), and a lower correlation between ALPP and smooth muscle atrophy (r=0.85).

Apoptosis: The results from the in situ analysis of apoptosis in the urethra and bladder tissue specimens show that the number of apoptotic cells in the urethra and bladder was significantly higher in the urethral detachment groups than in the control animals. At early time points, most apoptotic cells were identified in the epithelium and submucosa. With time, apoptosis was more prominent in the submucosa and muscle layers. These changes were seen throughout the bladder tissue and were not localized to a particular anatomic bladder region. There was no difference in the number of apoptotic cells between the preoperative controls and the sham operated animals.

Innervation: Neurons were identified using the neuronal-specific marker PGP 9.5. Compared to the preoperative control animals, there was a time dependent loss of neuronal content. There was no difference between the preoperative controls and the sham operated animals.

Experimental Results and Discussion: Stress urinary incompetence is characterized by involuntary urine loss due to an increase in abdominal pressure. The etiology of SUI is poorly understood but is likely multifactorial. Although loss of anatomic support due to vaginal deliveries appears to play an important role in its development, other changes seen with aging also contribute to the development of an incompetent urethra. Such changes include atrophy of the skeletal rhabdosphincter, atrophy of the smooth muscle of the urethra, loss of neuronal mass, and hormonal changes seen with menopause. It has been clear that no single alteration but a combination of factors acting together cause SUI. Therefore, the development of reproducible and durable animal models will allow us to explore the pathophysiology of SUI and to develop new treatments for this condition.

The first animal model of stress urinary incontinence was developed in 1998 by Lin et al. (1998) Urology 52:143-151. This model attempts to simulate one of the known risk factors for the development of SUI, the trauma of vaginal delivery by vaginal balloon dilation of the female rat. The model has been further evaluated and modified to overcome limitations such as the relatively low rate of incontinence and the spontaneous restoration of continence with time. In the originally described model only 46% of animals were deemed incontinent 4 weeks after the procedure. The role of ovariectomy and pregnancy on the animal have been evaluated to analyze their effects on the model. When animals were ovariectomized and balloon dilated immediately after delivery incontinence rate was increased to 72% at 8 weeks but this was not durable. Sievert et al. (2001) J. Urol. 166:311-317. This same group was unable to demonstrate significant changes in modified leak point pressures in female rats after ovariectomy and vaginal balloon dilation. Resplande et al. (2002) J. Urol. 168:323. In addition, they reported changes in bladder dynamics with detrusor instability in 64% of their castrated and balloon distended animals. Resplande et al. (2002) supra. Kuo (2002) Urol. Int. 69:36, reported a spontaneous recovery in the animals. Thus, the original model reported by Lin et al. (1998) supra, has been criticized because the relatively low rate of incontinence, the difficulty of reproducibility shown by different investigators, the high rate of bladder dysfunction, and the relatively short durability. All these factors make this an unreliable model for the long term evaluation of SUI, especially the effects of intervention in restoration of normal urethral function. An additional concern is that the way by which this model causes incontinence is poorly understood but seems to be related to vaginal and overall pelvic ischemia leading to bladder and urethral dysfunction, and vaginal ischemia. Therefore, this is not an ideal model recreating the isolated urethral dysfunction that we see in the majority of women who present with SUI.

Apoptosis is a highly regulated process of cell death. Studies of human tissues have shown that the age dependent changes seen in the muscular composition of the urethra and rhabdosphincter are correlated to age related increases in apoptosis in these tissues and suggest a positive correlation between cellular apoptosis and external and intrinsic urethral sphincteric weakness in older patients. Strasser (1999) Lancet 354:918-919. Interestingly, the animal model reported herein also shows a time dependent increased in apoptosis which appears to be related to the observed time dependent smooth muscle and skeletal muscle atrophy seen in these animals. In addition, a concomitant time dependent decrease in the pan neuronal marker PGP9.5 was seen in the tissues of the incontinent animals after transabdominal urethrolysis.

In this experiment, the impact of transabdominal urethrolysis on urethral innervation, smooth muscle content, and urethral and bladder function was evaluated. As compared to existing models of SUI, transabdominal urethrolysis is reliable and long-lasting. ALPP in the presence of a non-intubated urethra and RUPP are reliable quantifiable measures of urethral dysfunction. RUPP provides a less subjective assessment by the examiner when compared to ALPP. The loss of anatomic support, muscle atrophy, and loss of innervation seen in the urethrolysis animal model parallels changes seen in the incompetent aged female urethra.

Experiment No. 2—In Vitro Leiomyogenic Differentiation

This experiment shows the ADSCs can be induced to differentiate into functional smooth muscle cells and that developmental markers are expressed on the differentiated cells.

Isolation and Culture of Multipotent PLA Cells: All cellware material used in this experiment was purchased from Fisher unless otherwise stated. PLA cells were isolated as described above. Briefly, adipose tissue was extensively washed with phosphate buffered saline (PBS), minced for 10 minutes with fine scissors, and enzymatically digested at 37° C. for 30 minutes with 0.075% Type IA collagenase (C-2674; Sigma, St. Louis, Mo.) in PBS. The digested adipose tissue was centrifuged at 1200 g for 5 minutes to obtain a cell pellet. The pellet was resuspended and passed through a 100 μm filter to remove debris. Cells were plated in control medium (Dulbecco's Modified Media, DMEM (Mediatech, Herndon, Va.); 10% fetal bovine serum (FBS), HyClone (Logan, Utah) and 1% from a 100× concentrated antibiotic-antimycotic solution, (Mediatech) at a density of $5 \times 10^6$ nucleated cells per 100 mm tissue culture dish. The cells cultured as described are referred as P0 cells. To expand the cells through successive passages, adherent cells were allowed to grown to near confluency, washed with PBS and harvested using 0.25% trypsin/1 m EDTA. The cells were re-plated 1:4 and allowed to grow again.

Smooth Muscle Differentiation: For smooth muscle differentiation, both the effect of the medium and the effect of the substrate in the induction of a differentiated phenotype were studied. To study the effect of the medium, cells were cultured either in control medium or in inductive medium (Medium MCDB 131 supplemented with 1% FBS plus 100 U/ml heparin). To study the effect of the substrate, cells were plated either in regular uncoated culture dishes or regular dishes coated with laminin. Both commercial (BIOCOAT®, Becton Dickinson, Bedford, Mass.) and house-made coated plates were used. For the last, the plates were coated with laminin (Invitrogen, Carlsbad, Calif.) at 5 μg/cm². For these studies, cells from passage 2 were harvested, plated in control medium at 5000 cells/cm² in regular and coated-dishes for 72 hours and then incubated in either commercial smooth muscle medium or control medium for an additional 6 weeks. The medium was replaced each 3-4 days. After that, the cells were used for characterization of their phenotype.

Immunohistochemistry and Western Blot: The immunohistochemistry was performed using a commercial kit (R.T.U. VECTASTAIN® ABC Kit, Vector Laboratories, Burlingame, Calif.). Briefly, the adherent cells were washed with PBS, air dried, and then fixed with acetone/methanol 1:1 for 5 minutes. If present, the endogenous biotin was blocked using the Avidin/Biotin Blocking Kit (Vector). Blocking of the nonspecific antibody binding sites was done by incubating the cells with 2% normal horse serum for 20 minutes. The cells were then incubated with the primary antibody for 30 minutes diluted in PBS (for antibodies and dilutions see Table 2, below). After washing (3×), the cells were incubated with the biotinylated secondary antibody for an additional 30 minutes, followed by a final incubation with the streptavidin-peroxidase complex. The peroxidase reaction was developed using the DAB substrate chromogen (DAB Substrate Kit, Vector). The cells were counterstained with Mayer's hematoxylin (Dako, Carpinteria, Calif.). The cells were examined using an optical microscopy (Carls Zeiss, Germany) equipped with SPOT digital imaging acquisition system (Diagnostic Instruments, Ml). Control experiments were performed using an irrelevant primary antibody.

For the immunoblot analysis, the cells were washed with PBS and the proteins extracted by treating the cells with lysis buffer for 10 minutes on ice at a concentration of $5 \times 10^7$ cells per ml of buffer. The lyses buffer was made with 1% triton in saline and a protease inhibitor cocktail (Calbiochem, San Diego, Calif.). Then, 20 μg of protein was loaded and separated on SDS polyacrilamide gels and blotted onto nitrocellulose membranes using standard protocols. Visualization of secondary antibody binding was performed by chemiluminescence using Western-Star protein detection kit (Tropix, Bedford, Ma.).

TABLE 2

Antibodies Used in Smooth Muscle Studies

| Antibody/Clone | Antigen | Dilution | Commercial Source |
|---|---|---|---|
| MAB3242 | Smoothelin | 1:100 | Chemicon |
| CALP | Calponin | 1:50 | Dako |
| 1A4 | Smooth muscle actin | 1:100 | Dako |
| hHCD | h-Caldesmon | 1:100 | Sigma |
| BTI anti-Myosin | Smooth muscle myosin heavy chain | 1:250 | Biomedical Technologies |
| CD 105 | Endoglin | 1:100 | Pharmingen |
| vWfactor | vWfactor | 1:200 | Dako |

All except BTI anti-myosin are monoclonals.

RNA Isolation and RT-PCR: All reagents used in this experiment were purchased from Promega (Madison, Wis.) unless otherwise stated. Total cellular RNA was isolated from cultures using RNeasy Kit (Qiagen, Calif.) as described in the manufacturer's booklet, and reverse transcribed using conventional protocols. Briefly, cDNA was synthesized from 1 μg of total RNA in a 25 μl reaction mixture containing 1× reverse transcriptase buffer (5×=250 mM Tris-HCl, 375 mM KCl, 15 mM $MgCl_2$, 50 mM DTT), dCTP, dGTP, dATP, dTTP each at 0.5 mM, 25 U RNAse inhibitor, 200 U M-MLV reverse transcriptase, and 25 pmol Oligo(dT)15 primer. Reaction time was at least 1 hour at 42° C. Aliquots (2 μl) of the total cDNA were amplified using PCR Master Mix (Promega) in a 25-μl reaction containing 10 pmol of 5' and 3' primer. All amplifications were performed in a Mastercycler thermal cycler (Eppendorf Scientific, Westbury, N.Y.) for 35 cycles after an initial denaturation step for 2 minutes at 94° C. The same reaction profile was used for all primers: 94° C. for 30s, 53° C. for 1 min, and 72° C. for 1. The PCR Primers sequences are listed in Table 3 (Seq. ID Nos. 1 to 14). Reaction products were analyzed by eletrophoresis of 10 μl aliquots in 1.5% agarose gels and the DNA fragments were visualized by ethidium bromide staining.

TABLE 3

Oligonucleotide Primers Used in PCR Reactions

| Target gene | upper | lower | Product size |
|---|---|---|---|
| SM22 | ATGGCCAACAAGGGTC C (11 mer) | CTTCAAAGAGGTCAAC AG (18 mer) | 349 bp |
| Smothelin | ATGGCGGACGAGGCCT TAG (19 mer) | CCTCAATCTCCTGAGC CC (18 mer) | 358 bp |

TABLE 3-continued

Oligonucleotide Primers Used in PCR Reactions

| Target gene | upper | lower | Product size |
|---|---|---|---|
| Caldesmon | AGATTGAAAGGCGAAG AGCA (20 mer) | TTCAAGCCAGCAGTTT CCTT (20 mer) | 397 bp |
| Myosin | GGACGACCTGGTTGTT GATT (20 mer) | GTAGCTGCTTGATGGC TTCC (20 mer) | 656 bp |
| Calponin | ATGTCCTCTGCTCACT TCA (19 mer) | TTTCCGCTCCTGCTTC TCT (19 mer) | 453 bp |
| α-Smactin | ACCCACAATGTCCCCA TCTA (20 mer) | TGATCCACATCTGCTG GAAG (20 mer) | 595 bp |
| β-actin | GTAGATGGGCACAGTG TGGG (20 mer) | ATGGATGATGATATCG CCGC (20 mer) | 500 bp |

Quantitative Real Time PCR: The expression of α-smooth muscle actin (ASMA), calponin and SM22 was quantified for all differentiation conditions described above. Total cellular RNA was reverse transcribed using TaqMan Gold RT-PCR kit for real-time PCR (Applied Biosystems, Foster City, Calif.). Quantitative real-time PCR was performed in an ABI 7000 Prism Sequence detection system. Primer and probe sequences were designed by the UCLA Sequencing Core Facility and synthesized by BioSource (Camarillo, Calif.) having a 5' fluorogenic probe 6FAM and a 3' quencher TAMRA. The values corresponding to the levels of gene expression of ASMA were normalized using the expression of human glyceraldehyde-3-phosphate dehydrogenase (GAPDH). Human GAPDH primers and probe (5'JOE and 3'TAMRA) were a kind gift from Dr. Mark Hedrick.

Clonal Analysis and Multilineage Differentiation: PLA clones were isolated either using cloning rings or through limiting dilution. Expanded clones were analyzed for leiomyogenic, osteogenic and adipogenic differentiation. For osteogenic differentiation, after culture expansion the cells were plated at 5000 cells/cm$^2$ and grown to a subconfluence state. Then, the medium was switched for DME supplemented with 10% FBS, 0.1 μM dexamethasone, 10 mM beta-glycerol phosphate (Calbiochem, San Diego, Calif.) and 50 μg/ml ascorbic acid-2-phosphate (Sigma). The cultures were fed twice a week and after 3 weeks the osteogenic potential was evaluated by the histochemical presence of alkaline phosphatase and mineralized extracellular matrix using standard protocols. For adipogenic differentiation, after the cells grew to subconfluence, the cells were cultured in medium consisting of DME/F12 50:50 mixture supplemented with 10% FBS, 0.5 mM isobutyl-methyxanthine (Calbiochem), 100 nM insulin (Sigma), I μM dexamethasone (Sigma) and 1 μM troglitazone for 3 days after which the cells were allowed to mature in DME/F12 containing 3% FBS. After two weeks under inductive environment, the lipid accumulation was detected by Oil Red O staining.

Experimental Results and Discussion—Growth Of Undifferentiated And Differentiated Cells: PLA cells at passage zero cultured in uncoated dishes and with control medium grew out to confluence forming a typical monolayer of polygonal cells, presenting a flat morphology and stress-fiber pattern with very few areas of overlapping. The same arrangement was observed both with P1 and P2 cells. When PLA cells were culture in the presence of laminin, the cells retracted and formed nodule-like structures leaving areas of the bottom sparsely populated. Occasionally, the nodule-like structures evolved to a "sphere-like formations" connected by long cellular processes. This organization was observed starting at the first week after plating and continued to develop up to 6 weeks. In the presence of differentiation medium in uncoated substratum, the cells proliferate in a lower rate compared to control medium but did not present the nodular formation. On the contrary, the cells formed a monolayer with a mixed population of elongated and large rounded cells. The cells cultured on coated surface and inductive medium presented the typical "hills and valleys" formation formed by spindle-shaped cells.

Neither spontaneous adipocytic differentiation (formation of lipid vacuoles within the cells) or apparent mineralization of the nodules (opaque aspect under phase contrast microcopy) was observed in any of the culture conditions studied as well.

Gene Expression and RT-PCR: For the gene expression studies, 6 well-know markers for the leiomyogenic differentiation were evaluated: ASMA, smoothelin, calponin, caldesmon, myosin heavy chain and SM22, in both undifferentiated and differentiated cells. Unexpectedly, mRNA for all genes except myosin heavy chain was found to be spontaneously transcribed in cultured PLA cells even at the stage P0. After culture in a permissive medium the expression for myosin heavy chain was also detected. Although it was not quantified, it is possible to observe that the band relative the amplification of the cDNA corresponding to the calponin is much weaker that the other markers analyzed. This was true at both both 2 and 6 week's time period.

Proteic Analysis: Expression of the proteic markers in the cultured cells was examined by immunostaining the undifferentiated and differentiated cells at 6 weeks after culture both in inductive and non-inductive culture conditions. Because the cells in some culture conditions grew up in multilayers, the positive cells were quantified through scoring of the number of positive cellular groups. For this, the positive groups were categorized relative the cell number into clusters—up to 50 positive cells and colonies—more than 50 cells. In the cells cultured under control conditions, immunoreactive clusters for ASMA, calponin and caldesmon were observed as well some rare individual cells reactive with anti-smoothelin. No colony was detected and neither clusters nor individual cells were identified to react with anti-myosin heavy chain. However, when the cells were culture in differentiation medium, the number of positive clusters for ASMA increased and the development of colonies was observed. Similar increase was also observed for calponin and caldesmon. However, no colony of cells reacting with anti-smoothelin was detected. Similar response was observed when cells were cultured in laminin. The results are summarized in Table 4.

TABLE 4

Immunoreactivity of the cultured cells.
Results are recorded as average numbers of positive cellular groups.

| Marker condition | | ASMA | Calponin | Caldesmon | Smoothelin |
|---|---|---|---|---|---|
| Uncoated | clusters | 10 | 4 | 4 | I5 cells |
| Control medium | colonies | 0 | 0 | 0 | 0 |
| Uncoated | clusters | 13.5 | 7.5 | 7 | 1 |
| Differ medium | colonies | 2.5 | 2 | 0.5 | 0 |
| Coated | clusters | 2.5 | 2.5 | 5.5 | 4 cells |
| Control medium | colonies | 0 | 0 | 0 | 0 |

TABLE 4-continued

Immunoreactivity of the cultured cells.
Results are recorded as average numbers of positive cellular groups.

| Marker | condition | ASMA | Calponin | Caldesmon | Smoothelin |
|---|---|---|---|---|---|
| Coated | clusters | 13 | 11 | 8 | 2.5 |
| Differ medium | colonies | 3 | 2.5 | 0 | 0 |

Western blot analyses were performed to assess expression of ASMA protein, a marker common to all smooth muscle cells. Results showed that ASMA increased in the differentiated cells.

Quantitative PCR: Quantification of ASMA, SM22 and calponin expression using real-time PCR confirmed an increase in gene expression compared to non-induced cells both at population and clonal levels. At populational level, the most dramatic effect was observed on the expression of calponin which induction resulted in a increase of approximate 9-fold vs. control. It is interesting to note that this increase was lower when cells were cultured onto laminin-coated substrate (5-fold). This phenomena was also observed relative the expression of ASMA (2.5-fold vs 1.5-fold) and SM22 (4-fold vs 2.6).

PLA Clonal Analysis: To confirm the phenomena of differentiation and not only differential survival of specific progenitors, isolated cells from passage P0 were cloned either using clonal rings or limiting dilution. 11 clones were further examined for the expression of the smooth muscle-characteristic genes. All of the 11 clones were found to express mRNA for ASMA and caldesmon. SM22 mRNA was found in 10 and smoothelin was found in 8 out of the 11 clones. None of these clones were found to express mRNA for ASMA and caldesmon in non-inductive conditions as evidenced by RT-PCR. A very weakly band correspondent to mRNA of myosin heavy chain was observed in two of the clones. Thus, to test the induction of smooth muscle markers, clones with the ASMA (+), SM22(+), smoothelin(+), caldesmon(+), calponin(−) and myosin heavy chain(−) mRNA phenotype were chosen. Consistent with the differentiation process, clonal analysis showed that the expression of smooth muscle-specific genes and proteins is augmented when non-differentiated cells are cultured in permissive conditions that favor the leiomyogenic process. Real-time PCR analyses showed that, an augment of ASMA, calponin and SM22 gene expression is also induced at clonal level by the differentiation medium. Although not as high as at population level, the expression of SM22, calponin and ASMA augmented by approximate 1.5, 1.1 and 1.7-fold. To assess lineage plasticity at clonal level, isolated clones were subjected to osteogenic and adipogenic differentiation. Cells that underwent leiomyogenic differentiation were shown to possess potential for osteogenic and adipogenic differentiation, thus reinforcing the presence of multilineage precursors within the adipose tissue.

This experiment demonstrates that ADSCs cultured in permissive conditions possess the ability to undergo phenotypic and genotypic changes consistent with those observed during leiomyogenic differentiation. ADSCs cultured on uncoated dishes and in control medium formed a typical monolayer of flat cells. On laminin, the cells were characterized by aggregation into layered nodules that occasionally evolved to "spheres"—connected by spindle-like structures. In the presence of both laminin and heparin, the cells showed the "hills and valley" growth pattern characteristic of smooth muscle cells.

Although, ASMA is an early marker of developing smooth muscle, its expression is not restricted to smooth muscle. Thus, to characterize leiomyogenic differentiation, the expression of myosin heavy chain (MHC), caldesmon, SM22, calponin and smoothelin were also evaluated. These markers are highly restricted to differentiated smooth muscle and smoothelin is not detected in any other cell type. At gene level, unexpected it was discovered that ADCs spontaneously express all of the genes mentioned above but myosin heavy chain. However, MHC was induced upon differentiation. Since the cells were expressing the smooth muscle markers before the differentiation process, real time PCR was performed to quantify the gene expression of ASMA, calponin and SM22. At population level, an increase in gene expression of all markers analyzed was observed. This phenomena was also observed at proteic level. Immunohistochemistry studies showed that usually the positive cells for the markers analyzed were not evenly distributed around the culture vessel. Rather, the positive cells usually present a colony-formation pattern. Because of this, the number of colonies and clusters rather the percentage of positive cells were scored. Colonies of ASMA+ and calponin+ were more frequent observed than caldesmon+ colonies. Colonies were observed only after induction of differentiation in inductive medium. In the other hand, any cluster or colony of smoothelin positive cells was observed.

To ascertain that the induction of smooth muscle markers was due to differentiation and not because the culture conditions were selecting the smooth muscle cells originally present in the aspirates, the differentiation process was evaluated at clonal level. Differentiation at clonal level but in a less extension than heterogeneous cultures. Some of the soluble factors know to modulate smooth muscle cells are TGFβ-1, platelet derived growth factor, retinoic acid, interleukin 1 and ascorbic. Some of these factors are known to be produced by endothelial cells—one of the cell types identified in ADCs cultures.

Experiment No. 3—Regional Adipose-Derived Stem Cells

This experiment demonstrates that the origin of adipose tissue containing ADSCs affects proliferation and differentiation capacity in female rat adipose-derived multipotential cells. Inguinal, retroperitoneal and gongal adipose tissue contain populations of PLA cells with the capacity to differentiate into multiple cell types. These are regional different in cell morphology, growth and differentiation capacity.

Cell Harvest: Female Sprague-Dawley rats were anesthetized with Ketamine (50 mg/mL)) and Xylazine, shaved, and prepared with standard sterile technique as outlined by the Department of Laboratory Animal Medicine at the University of California. The inguinal (the inguinal subcutaneous, by carefully dissecting all fat in the inguinal region up to a horizontal line parallel to the xyphoid cartilage), gondal retroperitoneal(the retroperitoneal separating the perirenal fat) fat pads were then excised, finely minced, and incubated in 100-mm tissue culture plates (Becton Dickinson, Franklin Lakes, N.J.) containing antibiotic media: DMEM (Mediatech, Hemdon, Va.), 30% antibioticantimycotic (Mediatech), and 0.5 mg of gentamicin (Gibco BRL, Grand Island, N.Y.) for 1 hour. The tissue was then rinsed three times in phosphate-buffered saline (Mediatech) for 5 minutes, followed by digestion with 0.075% collagenase (Sigma, St. Louis, Mo.) with vigorous shaking for 40 minutes at 37° C. Next, an equal volume of DMEM with 10% fetal bovine serum was added to neutralize the collagenase. The cells and adipose tissue were placed in a cell strainer to remove the large, undigested tissue fragments, allowing the cells to be retained in a 50 ml conical tube. This was followed by centrifugation at 1300 rpm (260 g) for 5 minutes and resuspension in Dulbecco modified Eagle medium with 10% fetal bovine serum. Cell count and cell viability were determined with trypan blue exclusion. Rat adipose-derived stem cells were plated at a concentration of $10^6$ cells per 100-mm$^2$ tissue culture plate.

Cell Growth Kinetic Study: 5000 cells were plated in 35 mm dishes and at the indicated times the cells were harvested and counted using a hemacytometer and the viabilities were determined using trypan blue. Analysis of density vs. proliferation was achieved by plating different densities of cells in control media and after 14 days the cells were harvested and counted using the same technique mentioned above.

Colony-Forming Cell Assay: Cells were plated at 100, 200 and 1000 cells per 100 mm dish and cultured for in control media. The cultures were then fixed, stained with 1% crystal violet and counted at day 14 using an inverted light microscope. Colonies containing 50 cells or more but diameter<4 mm were scored as regular colonies. Colonies with ≧4 mm diameter were defined as HPP-CFC.

Flow Cytometry: Cells were plated at $10^3$ cells/cm$^2$ and cultured until cells reached subconfluency. For intracellular staining, cells were permeabilized with ethanol for 30 minute and incubated with monoclonal antibodies. After washing, staining with a secondary FITC-conjugated IgG goat-anti-mouse antibody (Chemicon, Temecula, Calif.) was performed for 30 minutes. Forward and side scatter gates were set to exclude debris and 10,000 gated events were counted per sample. Corresponding isotype and positive controls were performed for each antibody. Cells were analyzed with the flow cytometer FACS-Calibur (Becton Dickinson Immunocytometry Systems, San Jose, Calif.) and data were analyzed with the CELL QUEST software program (Becton Dickinson Immunocytometry Systems, San Jose, Calif.).

Adipogenic Differentiation: Cells are trypsinized and replated in basal medium at concentration of 5000 cells/cm$^2$ until approximately 70% confluency. Then, the medium is shifted for adipogenic medium consisting of DME/F12 50:50 mixture (basal medium) supplemented with 10% fetal bovine serum, 0.5 mM IMEX (Sigma), 1 µM insulin (Sigma), 200 µM indomethacin. (Sigma). After 2 weeks the cells are analyzed for the presence of lipidfilled vacuoles and enumerated through staining with solution of Oil red O (Sigma).

Osteogenic Differentiation: After culture expansion to three passages, the cells were trypsinized and replated onto 6-well tissue culture plates at $10^3$ cells per well. Cells were allowed to adhere and grow for 3 days to confluency, and then the media were replaced with osteogenic media containing Dulbecco modified Eagle medium with 10% fetal bovine serum, 0.1 µM dexamethasone (Sigma), 10 mM (β-glycerol phosphate (Sigma), and 50 µg/ml ascorbic acid-2-phosphate (Sigma). The media were changed every 3 days. Osteogenesis was assessed by von Kossa staining and alkaline phosphatase activity assays at 4 weeks after initial osteogenic induction. Also then expression of alkaline phosphatase and the levels of calcium were analyzed.

Alkaline Phosphatase Activity: Cells in 6-well plates were rinsed with phosphate-buffered saline and were incubated at 37° C. in 0.05 M Tris-HCl, pH 9 (Gibco BRL), containing 1 mg/ml Fast Red TR salt (Sigma) and 1% volume of a 50-mg/ml solution of naphthol AS-BI phosphate (Sigma) dissolved in dimethyl sulfoxide. After 30 minutes, an equal volume of 8% paraformaldehyde was added to fix the cells at room temperature for 10 minutes, followed by rinsing in distilled water. Positive alkaline phosphatase activity, which is indicative of osteoblastic differentiation, was detected as a red stain.

Von Kossa Staining: Cells in 6-well plates were rinsed with phosphate-buffered saline and were fixed in 4% paraformaldehyde for 1 hour. The cells were then incubated in 5% silver nitrate for 30 minutes in the dark, followed by rinsing with distilled water and exposure to ultraviolet light for 1 hour. Secretion of calcified extracellular matrix was observed as black nodules with von Kossa staining. Images were taken with a Zeiss Axioskop II microscope (Carl Zeiss Inc., Thornwood, N.J.) and Spot camera software (Diagnostic Instruments Inc., Sterling Heights, Mich.). Representative images were digitally captured under the microscope at low magnification (40x) from four different samples at each time point.

Smooth Muscle Differentiation: For smooth muscle differentiation, cells were cultured either in control medium (CM): Deubelcco's modified Eagle medium (Mediatech, Herndon, Va.) with 10% fetal bovine serum (HyClone, Logan, Utah), and 1% of antibiotic-antimycotic (Penicilin G 10,000 u/ml, Amphotericin B 25 ug/ml, Streptomicin 10,000 ug/ml) (Mediatech, Herndon, Va.) and our house-made made medium (SMDZ): Medium MCDB 131 (Sigma, Ml), supplemented with 2% FBS plus 200 U/ml heparin (VWR), for an additional 6 weeks. The medium was replaced each 3-4 days. After culture, the cells will be characterized relative their smooth muscle related-protein and gene expression. Relative the protein profile, the differentiation towards the smooth muscle pathway will be analyzed through expression of the alfa-smooth muscle actin, calponin and myosin heavy chain which are typically expressed by mature smooth muscle cells. These proteins were revealed through immunohistochemistry and Western blot.

Immunohistochemistry: The immunohistochemistry was performed using a commercial kit (R.T.U. VECTASTAIN® ABC Kit, Vector Laboratories, and Burlingame, Calif.). Briefly, the adherent cells were washed with PBS, air dried, and then fixed with acetone/methanol 1:1 for 5 minutes. If present, the endogenous biotin was blocked using the Avidin/Biotin Blocking Kit (Vector). Blocking of the nonspecific antibody binding sites was done by incubating the cells with 2% normal horse serum for 20 minutes. The cells were then incubated with the primary antibody for 30 minutes diluted in PBS (for antibodies and dilutions see Table 3). After washing (3x), the cells were then incubated with the biotinylated secondary antibody for an additional 30 minutes, followed by a final incubation with the streptavidin-peroxidase complex. The peroxidase reaction was developed using the DAB substrate chromogen (DAB Substrate Kit, Vector). The cells were counterstained with Mayer's hematoxylin (Dako, Carpinteria, Calif.). The cells were examined using an optical microscopy (Cads Zeiss, Germany) equipped with SPOT digital imaging acquisition system (Diagnostic Instruments, MI). Control experiments were performed using an irrelevant primary antibody.

Western Blot: For the Western Blot analysis, the cells were washed with PBS and the proteins extracted by treating the cells with lysis buffer for 10 minutes on ice at a concentration of $5\times10^7$ cells per ml of buffer. The lyses buffer was made with 1% triton in saline and a protease inhibitor cocktail (Calbiochem, San Diego, Calif.). Then, 20 µg of protein was loaded and separated on SDS polyacrilamide gels and blotted onto nitrocellulose membranes using standard protocols. Visualization of secondary antibody binding was performed by chemiluminescence using Western-Star protein detection kit (Tropix, Bedford, Mass.). Quantification was done by scanning of the immunoblots on STROM 860 (Amersham Pharmacia Biotech) using ImageQuant software (NIH image J).

Anti-calponin antibody (CALP; Dako) was added at a diluted concentration of 1:50; anti-ASMA antibody (1A4; Dako) was added at a diluted concentration of 1:100 and anti-smooth muscle myosin heavy chain (BTI anti-myosin antibody; Biomedical Technologies) was added at a dilution concentration of 1:250.

Experimental Results and Discussion: The average number of cells obtained per gram of fat after processing was $111 \times 10^4$, $147.3 \times 10^4$ and $191.5 \times 10^4$ cells for inguinal, retroperitoneal and gondal sites, respectively. When plated, the rat progenitor cells both appeared as a heterogeneous population of fibroblast-like cells. (morphology picture), gondal site showed a bigger cell. Although the doubling time varied between rats, a consistent trend was observed with respect to the source of the PLAs. The cells derived from the gondal fat depot always presented a longer doubling time than the inguinal and retroperitoneal depots. The average calculated doubling time for the inguinal, retroperitoneal and gondal were 25.85 hours, 31.9 hours and 41.47 hours, respectively. Following isolation, an initial lag time of 2-3 days was observed in 3 fat depots cell cultures, then the cells entered a proliferation phase within 48 hours. However, different than rat bone marrow mesenchymal stem cells, the proliferation of rat PLAs appears to have a positive correlation with a higher density plating.

Colony-Forming Cell Assay: The CFC assay was completed by plating 100, 200 and 1000 cells per 100 mm dish. In 14 days the cells were stained with crystal violet and the dishes were analyzed to determine if the fat depots contained cells with CFC properties and if they did then further analyzing was performed to determine if they were high proliferative colonies. For each fat depot, the numbers of colonies in was counted. 8 HPP-CFCs and 7.5 colonies in 1000 PLA cells supported the growth of inguinal CFC better than retroperitoneal and gonadal.

Characterization of 3 depots PLA cell by FACS Based on the FSC/SSC Profile: Physical parameters were used to characterize the 3 depots of PLA cells: 1) forward scatter (FSC), representing cell size, and 2) side scatter (SSC) representing cellular granularity. Because FSC originates in particles with diameters that are larger than the wavelength of the probing light, the FSC serves as an indirect measure of overall cell size. In contrast, the SSC is generated by light scattered by discreet elements whose size is smaller than the wavelength of the probing beam, and thus SSC represents a direct measure of the cell's granularity. There was a a clear distinction between the cell populations. The gondal cells elicited FSC and SSC that were higher respectively, than those generated by the inguinal and retroperitoneal cells. The FSC results imply that the gondal cells are much bigger than the inguinal and retroperitoneal cells across the whole population spectrum, this also confirmed by observations under microscope. Also the SSC results further imply that gondal cells have higher cytosol granularity. Taken together, larger particles observed by the light scatter parameters (FSC and SSC) in gondal site. These data also support the notion that with a smaller size correlate with a lower cytosolic granularity. In conclusion, FACS analyses showed that cultures originated from the gondal site present a higher proportion of larger and probably more mature cells.

Differentiation of Rat PLA Cells: To determine whether rat PLA cells, like PLA cells from human, are capable of differentiation to multiple cell types, rat cell from 3 depots were placed into induction media specific for the generation of adipocytes, osteocytes, and SMC differentiation.

To generate adipocytes, rat PLA cells from each fat depot were plated at concentration of 5000 cells/cm² and left to grown up to sub confluence stage. Then the regular medium was shifted for differentiation media and the cultures another 14 days. The culture condition that we studied was the following: DME/F12 50:50 mixture as basal media supplemented with 10% fetal bovine serum, 100 nM insulin, 1µM dexamethasone, 0.2 mM IMEX and 1 µM troglitazone as PPARy agoniSt. Under these conditions the first droplets of lipids become visible around 7 days after induction and the lipid vacuoles continued to develop over time, coalesced and eventually filled the cell. These adipocytes remained healthy in culture for 2 weeks. After 2 weeks the cells were analyzed for the presence of lipid-filled vacuoles through staining with solution of Oil Red O. Respect to adipogenic differentiation, the cells originating from the retroperitoneal site originated, an average of 17% of lipid-containing cells while this percentage was dramatically reduced in the cultures originated both from inguinal (6.1%) and gondal (2.20%) sites.

Differentiation of rat 3 depots PLA cell into osteoblasts is induced in vitro by treating cells with low concentrations of ascorbic acid, β-glycerophosphate, and dexamethasone. Early differentiation of these cells into immature osteoblasts is characterized by AP enzyme activity. Although AP expression is dramatically unregulated in osteogenic tissues, its expression has been observed in several nonosteogeniccell types and tissues such as cartilage, liver, and kidney. Therefore, AP expression is frequently used, in conjunction with other osteogenic-specific markers, as an indicator of osteogenesis. One such indicator is the formation of a calcified extracellular matrix (ECM). Mature osteoblasts secrete a collagen I-rich ECM that becomes calcified during the later stages of differentiation. Therefore, to confirm osteogenic differentiation, calcification of the ECM matrix was assessed in PLA cells using a von Kossa stain. Rat PLA cells cells originated from inguinal and retroperitoneal, gondal placed in osteogenic media exhibited changes in cell structure after 4 days in culture. The cells changed from an elongated fibroblastic appearance to a rounder, more cubical shape. Islands of extracellular matrix were secreted from these cells 7 days after osteogenic induction. The cells stained positively for endogenous alkaline phosphatase activity after 2 weeks of culture in osteogenic media and formed mineralized nodular structures, as confirmed by von Kossa staining. Quantitative assays revealed a 3- and 1.2-fold increase in alkaline phosphatase activity in inguinal and retroperitoneal fat depots, and calcium accumulation were evident after 4 week and increased 1.5 and 1.3 fold compare to the control medium. Interesting, the cell originated from gondal site express a distinguished characterize. Under the control medium the gondal express high level of endogenous alkaline phosphatase activity, after treat with OM, was decreased the alkaline phosphatase activity. Same result was confirmed by quantitative assays for alkaline phosphatase activity. But the gondal cell staining still positively for von kossa staining and calcium quantification assay showed that under the osteogenic induction the calcium accumulation was increased 1.3 fold compare to the control medium. Take together, the expression of AP and calcium accumulation by rat PLA cell strongly suggest that higher osteogenic capacity were seen with cells isolated from the inguinal and retroperitoneal depots than gondal depot.

The PLA cells processed from human adipose tissue is a heterogenous population including a population of mesodermal or mesenchymal cells with low contamination by endothelial cells, pericytes, and smooth muscle cells (29.2%). However, no literature regarding rat has been published. To determine PLA smooth muscle composition quantitatively, PLA cells samples were analyzed by flow cytometry using the early smooth muscle markers described above. PLA cells were incubated with monoclonal antibodies to smooth muscle actin, and calponin. Cell viability was assessed by using propidium iodide and samples were corrected for viability, nonspecific fluorescence, and auto fluorescence. Cytometry data was collected from 3 depots of at passage 2-4, and the number of positive events for each cell-specific marker was expressed as a percentage of the total PLA cell number. There was some variation between rats, but always compare to the inguinal retroperitoneal cell gondal site always express more ASMA calponin.

To differentiation of rat 3 depots PLA cell into smooth muscle cell, we cultured cells with the control medium, house made medium. Cell differentiation was determined by morphology, immunohistochemistry and Western blotting for smooth muscle markers. After 6 weeks in differentiation conditions, cell morphology began to change from the fibroblast like shape typical of PLA cells to flatter and broadened and less tightly packed polygonal cell. However the cell distribution did not present significant differences from the control cells. No predominantly smooth muscle-appearing cells with a "hill and valley" morphology were observed.

To additionally evaluate phenotype, the expression of smooth muscle cell-specific antibodies, myosin heavy chain (MHC), ASMA and calponin (CAL) were analyzed by western blot. At 2 weeks, inguinal retroperitoneal PLA cells cultured with SMDS, SMDZ in petri dishes presented that smooth muscle actin (SMA) and calpionin (CD) were slightly increase compare to the cell cultured in CM in regular dish. MHC expression was not seen in either in CM or inductive medium. The gondal site PLA cells also presented expression of ASMA, CALP, however there were no obvious changes between CM and inductive medium. Distinct different from the other two depots, gondal site have heavy expression of MHC both in CM and in SDMZ at this time point.

At 6 weeks, when these inguinal and retroperitoneal cells were cultured with CM on regular petri coated culture dishes, the expression level of ASMA and calponin started to decrease. Also after 6 weeks induction, the MHC (the late marker of SMC) was induced in retro PLA under SMDZ. In the gondal site, after 6 weeks differentiation, these 3 SMC markers have dramatically decreased in differentiation medium compare to the CM.

The immunohistochemistry experiment which comparing the 3 sites PLA cells cultured with different medium and coated dish also confirmed the western blot data: when the inguinal retroperitoneal cells were cultured with control medium (DMEM), on uncoated dishes they presented ASMA and CALP an average of 30% respectively. The SMDS make the ASMA and calpinion in inguinal cell express slightly increase to 35% SMDZ medium make the ASMA calplin express reach to around 40-50%. Compare to regular dish, the expression of in collage and lamin matrix no difference with Petri dish. The gondal cell shows distinguished characterize than the other 2 depots. In control medium (DMEM), the ASMA, calplin express in gondal cell is almost 100% positive, in the SDMS medium make ASMA and CALP expression drop to around 30%. Compared to the control medium (DMEM), the SMDZ make the calplin in gondal cell just slightly decrease, the positive cell reached to 80%. Similarity with inguinal and retroperitoneal, there are no expression difference between different coated dish. At this time the positive stained cells presented a random distribution on the culture dishes.

In the present study, the cells obtained from distinct fat depots originating from adult rats were processed and analyzed for their relative growth kinetics, clonogenic capacity, scatter properties and differentiate ability. Although these 3 depot's cell have some similarities these 3 cellular factions are comprised of fibroblast-like cells that can be expand easily in vitro without the need for specific sera lots or media supplementation. Also consistent with that of human PLA cells, those cells from several rats maintained a linear growth rate. However, certain key differences among inguinal, retroperitoneal and gondal also were detected. The average doubling time for PLAs processed from inguinal, retroperitoneal and gonadal sites were 25.85 hours, 31.9 hours and 41.57 hours, respectively. Differences were also observed in the number of CFC's and scatter properties. The cell population isolated from the gonadal site presented the lowest number of CFCs and also presented the highest FSC compared to the other sites.

To determine whether rat fat pads contain adipose-derived multipotential cells that the resemble human adipose-derived stem cell and whether multilineage capacity are site specific, cells from 3 depots were differentiated toward the adipogenic, osteogenic lineages with appropriate medium supplementation. Following induction, differentiation was assessed using histology and immunohistochemistry. This study showed that the 3 depots cell have multi-lineage capacity but higher osteogenic capacity was seen with cells isolated from the inguinal depot while the population isolated from the retroperitoneal site presented the greatest number of fatty cells upon differentiation.

This is the first study to show smooth muscle differentiation capacity of rat fat pads characterized by expression of smooth muscle marker. Previous studies of smooth muscle cells differentiation and their phenotypic modulation indicated that SMCs express the contractile differentiated phenotype when they are not in a proliferate states. Heparin has been shown to prevent phenotypic modulation of SMCs, to decrease cellular proliferation rate as well as to induce smooth muscle marker expression. The medium MCDB 131 supplemented with 2% FBS plus 200 µg/ml heparin (SMDZ) was used in this study. The western blot and immunohistochemistry data has showed that the PLA cells processed from inguinal and retroperitoneal adipose tissue after 6 weeks induction, all the smooth muscle marker were increased especially the late marker of differentiation, myosin heavy chain which present only in contractile smooth muscle cells start to express. In addition to the medium, prior studies suggested that the extracellular matrix plays a role in differentiation by modulating the phenotypic differentiation of SMCs. In this experiment; however, laminin appeared to only increase the induction of mysion heavy chain in inguinal derived cells and collage I only have effect on the retroperitoneal derived cell. Besides the induction of a late marker, the media rather than matrix seemed to be the predominant differentiating factor. The gondal-derived cell have distinguished even undifferentiation cells expressed significant levels of smooth muscle actin and calponin the media and matrix failed to induce the smooth muscle marker expression. Compared to the inguinal and retroperitoneal site, the gondal-derived cells have more mature cells which lost the capacity to differentiation into smooth muscle cell.

These results point to intrinsic site-related differences between PLAs. Inguinal and retroperitoneal derived PLA cell have higher proliferation rate and multinleage differentiation capacity. The gondal derived cell presented the lowest proliferation rate, seems to more mature, and have the lowest osteogenic, adipogenic capacity, and have lost smooth muscle differentiation capacity.

In conclusion, not only do inguinal, retropertioneal and gondal fat tissue differ in location, they also display differences in the metabolic and growth rates and differences of differentiation capacity. In rats, regional adipose-tissue growth (through an increase in adipocyte size or number) develops in a depot-specific manner. Like the adipose tissue accumulation, since the adipose tissue are partially under autocrine/paracrine regulation, the PLA cells which isolated from different adipose regions also regulated their growth patterns by the interaction of genetics, local factors, systemic factors, vascularization, and degree of innervation by the sympathetic nervous system. Local region-specific regulatory control factors include angiotensinogen, interleukin-6, tumor necrosis factor-α, insulin-like growth factor-I (IGF-I), and leptin.

Experiment No. 4—Study of Gender Effect on Differentiation Potential

This experiment evaluates the differences between male and female rats on the differentation potential towards mesenchymal lineages by PLA cells isolated from distinct fat pads.

Cell Harvest: 3 males and 3 females Sprague-Dawley rats are anesthetized and prepared with standard sterile technique as outlined by the Division of Laboratory Animal Medicine at UCLA. The inguinal, epididimal or retroperitoneal fat pads are excised, finely minced and incubated with 0.075% collagenase solution (Sigma, St. Louis, Mo.) for 60 minutes at 37° C. After incubation, the tissues is washed and passaged through a cell strainer of 100 μm mesh to remove the undigested tissue fragments. The cells are then centrifuged at 400 g for 5 minutes and re-suspended in control medium DMEM (Mediatech, Herndon, Va.) with 10% fetal bovine serum (HyClone, Logan, Utah) and 1% antibiotic/antimycotic solution (Mediatech)) and let to expand. After harvest with trypsin/EDTA solution (Mediatech), the cells are plated for culture under differentiation conditions.

Leiomyogenic Differentiation: For smooth muscle differentiation, cells from passage 1 are plated onto laminin—coated substratum at 5000 cells/cm$^2$ and let to grow for 48 hours in control medium. The medium then is shifted for inductive medium (Medium MCDB 131 supplemented with 1% FBS plus 100 U/ml heparin (VWR)) and the cells are cultured for an additional 6 weeks period with biweekly feeding. After culture, the cells are characterized relative their smooth muscle related-protein and gene expression. Using methods and markers discussed above. (See Experiment Nos. 2 and 3, above). Differentiation towards the smooth muscle pathway is analyzed through expression of the alfa-smooth muscle actin, calponin, caldesmon, myosin heavy chain and smoothelin which are typically expressed by mature smooth muscle cells.

The multipotential nature of the cells in study can be verified through the capacity of the cells to respond also to adipogenic, osteogenic and chondrogenic stimulus throughout the study, using the following induction medium or alternatively other inductive conditions known in the art.

Adipogenic Differentiation: Cells from passage 1 are trypsinized and replated in control medium at concentration of 5000 cells/cm$^2$ until approximately 70% confluency. Then, the medium is shifted for adipogenic medium consisting of DME (basal medium) supplemented with 10% fetal bovine serum, 0.5 mM IMEX (Sigma), 1 μM insulin (Sigma), 200 μM indomethacin.(Sigma). After 2 weeks the cells are analyzed for the presence of lipid-filled vacuolos and enumerated through staining with solution of Oil red O (Sigma).

Osteogenic Differentiation: After culture expansion, P1 cells are plated in control medium at 5000 cells/cm$^2$ and let to grow to sub-confluence state. Cells are then incubated with osteogenic medium consisting of DMEM supplemented with 10% fetal bovine serum, 0.1 μM dexamethsone (Sigma), 10 mM beta-glycerol phosphate (Calbiochem, San Diego, Calif.), and 50 μg/ml ascorbic acid-2-phosphate (Sigma). The cultures are feed twice a week with fresh medium. After 3 weeks, the potential osteogenic is evaluated measuring the presence and activity of the enzyme alkaline phosphatase and analyzing the mineralization degree of the extracellular matrix (through Von Kossa staining).

Chondrogenic Differentiation: Chondrogenic differentiation is induced through culture of aggregates. For this, cells at passage 1 are trypsinized, and 200000 cells are placed into 15-ml polypropylene tubes containing 0.5 ml of chondrogenic medium and centrifuged at 400 g for 2 minutes. Chondrogenic medium consists of DMEM supplemented with 1% fetal bovine serum, 10 mg/ml transforming growth factor-β 1 (TGFβ-1) (R&D Systems, Minneapolis, Minn.), 6.25 μg/ml insulin (Sigma) and 6.25 μg/ml of transferrin (Sigma). Chondrogenesis is assessed using Alcian Blue staining and immunohistochemistry for detection of collagen II.

Experiment No. 5—ADSCs can Differentiate into Smooth Muscle In Vivo

This study shows that PLA differentiate into smooth muscle in vivo, and is therefore useful to reconstitute smooth muscle in a patient.

Isolation and Culture of PLA Cells: Lipoaspirate from human subjects undergoing liposuction was obtained and processed as described above. PLA was seeded into 100 mm$^2$ culture dishes at a density of 5×10$^5$ cells per plate and split routinely when nearing confluence to prevent spontaneous differentiation. 300 ml of lipoaspirate yielded a primary culture of 2×10$^8$ PLA cells.

Cell Labeling and Harvest: Cultured PLA cells at passage 3 or less were rinsed and incubated with 1:200 dilution of dialkylcarbocyanine fluorescent solution (Vybrant DiI; Molecular Probes, Eugene, Oreg.,) in accordance with manufacturer's protocol then rinsed and cultured in control media until harvest (24 hours). For bromodeoxyuridine (BrdU; Sigma, St. Louis, Mo.) labeling, cells were incubated in 10 μM BrdU solution in media for 24 hours. Labeled PLA cells were trypsinized (Mediatech, Herndon, Va.), centrifuged, and suspended in Hank's balanced salt solution (HBSS; Sigma, St. Louis, Mo.).

Cell Injection: Animal studies were performed in accordance to guidelines set forth by the Animal Research Committee at UCLA. In vivo survival of the PLA cells within urethra and bladder was assessed in adult female Rnu athymic rats (n=8, NIH-Foxn1mu, Charles River, Wilmington, Mass.) weighing 200-250 grams and adult female C.B.-17 SCID mice (n=6; 45-60 days-old; C.B.-17//crCrl, Taconic Farms, Oxnard, Calif.). Animals were anesthetized with 2% isoflurane. A supra-pubic incision was made and a 50 μl Hamilton microsyringe with a 22 gauge Hamilton needle (Fisher Hamilton, Pittsburg, Pa.) was used to inject a total of 10 μl (1×10$^6$ cells) of the PLA cell suspension into the anterior mid urethra (n=8 rats) and into the anterior bladder wall (n=8 rats; n=6 mice). Injection into the urethra was only technically feasible in the rat. Localization of the cells within the wall was confirmed by visualization of a raised wheal under the serosal surface. An additional group of nude rats (n=8) received sham injections of HBSS alone into the urethra and bladder as negative control.

Tissue Procurement: Rats (n=2 per group/time point) were sacrificed at 2, 4, 8 and 12 weeks after injection. SCID mice (n=3 per time point) were sacrificed at 4 and 8 weeks post-operatively. The bladder was separated from the urethra at the bladder neck and sectioned transversely. The urethra was step-sectioned transversely to include the bladder neck, mid urethral injection site, and distal meatus. All specimens were formalin fixed and paraffin embedded. Four micron thick tissue sections were cut for histological examination.

Cell Tracking and Sample Analysis: Excised tissues were analyzed for the presence of viable PLA cells. Three tracking methods were used to localized the cells and determine cell survival: 1) DiI, 2) human Alu DNA sequence, and 3) BrdU. All slides were photographed and the images digitalized using a color digital camera and imaging software (Spot v2.1, Diagnostic Instruments, Sterling Heights, Mich.).

Localization of the DiI labeled PLA cells was determined using an epifluorescence microscope (Carl Zeiss, Oberkochen, Germany) filtered for excitation/emission at 546/590nm. Human genomic sequence of the injected PLA cells was tracked in the animal host tissue using in-situ hybridization for the human Alu DNA (Innogenex, San Ramon, Calif.). BrdU labeling was identified using a streptadivin-biotin BrdU staining kit (Oncogene, Boston, Mass.).

Smooth muscle phenotype was assessed using immunostaining for alpha-smooth muscle actin (ASMA, Sigma, ST. St. Louis, Mo.). Evaluation was performed with epifluorecence microscopy. Cell nuclei were counterstained with DAPI, and PLA cells were simultaneously identified by DiI as described above.

Experimental Results and Discussion—PLA Cell Culture and In Vitro Cell Labeling: The PLA cells were easily cultured and passed with a population doubling time of 60 hours. PLAs were capable of pluripotent lineage differentiation under lineage specific conditions in vitro.

The BrdU label was incorporated into 40% of the cellular DNA and the DiI into 100% of the cells.

Animal Studies: Animals underwent injection of HBSS alone (sham group; n=8 rats) or injection of $1\times10^6$ PLA cells suspended in HBSS (experimental group; n=8 rats and 6 mice) into the mid urethra and anterior bladder. All animals tolerated the procedure without complications.

On histological analysis, the human PLA cells were identified within the host tissues at up to 12 weeks post-injection as verified by localization of DiI, BrdU and Alu staining. At 2 weeks post-injection, a dense nodule of PLA cells was histologically visible at the site of injection in the experimental animals. The sham animals had normal bladder and urethral histology. By 4 weeks, the PLA cells had begun to disperse throughout the urethral and bladder smooth muscle; however, smaller PLA cell nodules remained nearest the injection site. The PLA nuclei demonstrated rounded morphology at 2-4 weeks post-injection. At 8 and 12 weeks post-operatively, there was no longer any histological evidence of PLA clumping at the injection sites and the cells were dispersed evenly within the local SM and lamina propria without significant losses in the overall cell number and the nuclei demonstrated a fusiform shape.

Triple staining of the tissue sections for nuclei (DAPI), cell membrane (DiI) and ASMA (FITC), showed that the PLAs expressed ASMA at 8 weeks, suggesting the potential for smooth muscle differentiation in vivo.

This study shows that pluripotent human lipoaspirate cells can be easily procured and transplanted into the bladder and urethra. Two animal models were studied to show the viability of human PLA cells was not species dependent. In addition, injection into the urethra was only feasible in the rat because of the size restrictions of the mouse urethra. The injected PLA cells demonstrated phenotypic expression of smooth muscle markers in vivo, and they remained viable in the lower urinary tract for up to 12 weeks. Viable smooth muscle was subsequently confirmed at 6 months post-injection. The injected PLA cells transitioned from round to fusiform nuclei in vivo, consistent with transition from a proliferative cell phase into a contractile cell phase. In addition, the phenotypic markers of the injected PLA cells were consistent with early differentiation into SM, as the in vivo PLA cells showed expression of ASMA. ASMA is responsible for smooth muscle contraction, and it has been used as a marker of early SM differentiation.

Experimental No. 6—ADSCs for Bladder Reconstruction

The smooth muscle cells of diseased bladders have been shown to be abnormal, potentially limiting their use. This experiment shows that a tissue engineered bladder generated from smooth muscle cells differentiated from adipose derived stem cells.

Methods: Human lipoaspirate was processed to yield a culture of multipotent cells as described above. The ADSCs were labeled with DiI, cultured in a media conducive to smooth muscle differentiation, and seeded at a density of $1\times10^6$ cells per cm$^2$ onto mats electrospun from 85:15% PLGA. Six adult rats underwent partial cystectomy and bladder augmentation with a 1 cm$^2$ patch of engineered bladder; an additional 6 rats had primary closure of the bladder dome as control. Urodyanmic testing was performed pre- and post-operatively on all animals. Bladders were harvested at 1 and 2 weeks for histology.

Experimental Results and Discussion: ADSCs were negative for smooth muscle markers at the time of harvest. After 3 weeks in smooth muscle specific media, the ADSCs expressed myosin heavy chain (MHC), a late specific smooth muscle marker. The electrospun mats remained pliable and stable in culture for up to 4 weeks. The differentiated ADSCs adhered to the scaffold at 80% confluency and they maintained MHC expression for up to 4 weeks in vitro on the scaffold. See Table 5, below.

TABLE 5

In vivo Expression of Smooth Muscle Markers in ADSCs Injected into Bladder Wall

|  | 2 weeks | 4 weeks |
|---|---|---|
| α-SMA | YES | YES |
| calponin | NO | YES |
| MHC | NO | YES |

Bladders augmented with the engineered scaffolds had superior capacity and compliance compared to partial cystectomy (Table 6). The engineered bladder walls had progressive urothelial coverage along the luminal surface at 1 and 2 weeks in vivo. At 2 weeks, the bladder grafts had trace amounts of smooth muscle along the serosal surfaces.

Adipose derived stem cells can be differentiated into smooth muscle in vitro and maintain MHC expression on electrospun PLGA scaffolds for extended periods of time.

Bladder augmentation using scaffolds engineered from differentiated ADSCs results in improved bladder function compared to partial cystectomy.

TABLE 6

Urodynamic Results of Bladder Engineered From Electrospun PLGA and ADSCs

| | Normal Bladder | Partial Cystectomy | Tissue Engineered Bladder |
|---|---|---|---|
| Capacity (ml) | 1.8 | 1.1 | 1.7 |
| Compliance (μl/cm H$_2$O) | 90 | 30 | 80 |

Experiment No. 7—ADSC Formulation

This experiment demonstrates that ADSC can be delivered in situ in a variety of formulations.

Human adipose tissue obtained from patients undergoing elective cosmetic suction-assisted lipectomy was processed as described above. The cells were expanded two to three passages prior to adipocytic induction.

Adipocytic Induction: For adipogenesis, PLA cells were let to expand to confluent state in control medium, only after which they were exposed to adipogenic inducers. Media of two different compositions were used. One (referred to herein as "reference media" or "AM1") consisted of DME medium supplemented with 10% fetal bovine serum, 0.5 mM isobutyl-methyixanthine (IBMX), 1 μM dexamethasone, 10 μM insulin, 200 μM indomethacin and 1% antibiotic/antimycotic as described by Zuk et al. (2001), supra. The second media consisted of DME/F12 mixture (Mediatech) supplemented with 10% fetal bovine serum, 1 μM dexamethasone, 500 μM IBMX, 100 nM insulin and 1 μM troglitazone. This media is referred to herein as "AM2". Under AM1 culture, the adipogenic induction was carried out for 7 days with regular medium changes every 2-3 days. Under AM2, the induction was carried out for 3 days, after which the medium was shifted for DME/F12 with 3% fetal bovine serum for additional 7 days with regular feeding every 2-3 days. For transplantation, the cells were detached from the culture plates using trypsin/EDTA (Mediatech) and resuspended in the fibrinogen component of the fibrin-glue carrier.

Preparation of Fibrin Glue-Carrier: Fresh thrombin (Sigma, MO) and fibrinogen (Sigma) solutions were prepared from lyophilized reagents following the manufacturer instructions. To optimize the clot formation, several thrombin dilutions in 40 mM CaCl$_2$ were tested (1:2 to 1:10) and to evaluate cell distribution and final size of the nodule both low (10$^6$) and high cell number (10$^8$) were tested. The fibrin glue cellular nodules were prepared in 50 ml tubes mixing the same volume (300 μl) of fibrinogen solution (10 mg/ml in sterile 0.9% NaCl) containing the PLA cells and diluted thrombin solution. The resulting nodules were gently removed, measured and snap frozen for histological evaluation.

Animal Surgery: A total of eight NUDE/SCID mice (8-10 weeks old) were used for this study. To create a subcutaneous fibrin-glue nodule, both fibrinogen/cells and thrombinl/CaCl$_2$ components were allocated separated in two 1cc syringes, which were connected to a two-way dispenser for a gentle and slow delivery of the reagents at same time on the animal dorsum. Two nodules were created in each mouse—one with high cell number and the second with low cell number. After 4 and 8 weeks, the resulting nodules were removed and sectioned in two parts. One half was snap frozen and the other half was treated with osmic acid before being fixed in 10% formalin. For standard histology, conventional Hematoxilin/Eosin (HE) staining was performed in the frozen sections. For detection of fatty cells, both Oil Red O and Osmic acid staining were performed in frozen and paraffin sections, respectively, using the procedure and reagents described above.

Experimental Results and Discussion: Over the various tested titrations of thrombin, the most solid nodules with faster clot formation were observed to be those with thrombin/CaCl$_2$ ratio between 1:5 and 1:9. Nodules formed using ratios below 1:5 did not show a homogeneous clot formation presenting an aqueous phase around the clotted core of the nodule. Since similar results were obtained in the range of 1:5-1:9, a lower concentration of thrombin was used. The average size of the nodules containing 10$^8$ and 10$^6$ cells was 1.0+/−0.1 and 1.1+/−0.2 cm, respectively. In both cell concentrations, uniformly distribution of the PLAs cells throughout the nodule was observed.

In Vivo Grafting: In vivo nodule formation was successfully achieved in 13 out of 16 injections. There was no postoperative morbidity or mortality. The nodules were visible up to 8 weeks in the implanted site. Overall, the nodules harvested at 4 weeks presented an average size of 0.95+/−0.21 cm, which was slightly smaller than nodule size evaluated in vitro. At 8 weeks, the nodules had a decrease of about 50% in size. A significant difference on the size of the nodules relative the cell number seeded was not observed. The nodules containing 10$^6$ and 10$^8$ cells averaged 0.40+/−0.05 and 0.45+/−0.1 respectively at 8 weeks. Both at harvesting times of 4 and 8 weeks, the nodules appear to show signs of integration with the host tissues which is evidenced by the observation of grossly vascularization on top of the nodules. Vascularization was more prominent in nodules seeded with 10$^6$ cells instead of 10$^8$ cells.

Composition of the Implanted Nodules: HE staining and osmic acid staining of a typical low cell concentration nodule were performed at 4 weeks. At this time, fatty cells are observed randomly distributed around the nodule and the small lipids vacuolos indicate early adipogenic differentiaton. At 8 weeks, the nodules showed a reduced content of fibrin glue and bigger lipids droplets were now prevailing inside the cells, as is expected from more mature cells.

Optimization of the Adipogenic Differentiation: Cultured under the reference media, the first signs of adipogenesis were observed around the 7$^{th}$ day post-induction. At 10 days, an average of 66% of the cells stained positively with Oil Red O. Usually, the fat-containing cells presented multiple but small lipid droplets. No spontaneous adipogenesis was seen in cells cultured with control medium. In the presence of the PPARy agonist and the other inducers contained in AM2, a slightly higher rate of differentiation (73%) compared to the reference media was observed. A more significant contrast was observed at qualitative level. Lipid droplets appeared earlier (around the 5$^{th}$ day) in the cells cultured with AM2 and at 10 days the droplets were at least three times as big their counterparts in the cells cultured with AM1. The same effect was observed both in passages 1, 2 and 3 suggesting that the level of reactivity of the responsive cells does not change with successive rounds of passage.

Experiment No. 8—ADSC and Sex Hormones

This experiment demonstrates that sex hormones affect growth and differentiation of ADSC.

Sprague Dawley rats were used for all experiments described in this example. ADSCs from different fat depots (retroperitoneal, inguinal, and gonadal) from male and female animals were harvested as described supra. The cells were then compared in their growth kinetics and differentiation ability after exposure to estrogen or testosterone. Cells were plated at a concentration of $10^6$ cells per 100 mm$^2$ tissue culture plates. All cells were grown in culture medium and maintained at 37° C. and 5% $CO_2$.

Cell Growth & Kinetic Studies: Analysis of cell density versus proliferation was achieved by plating cells of the following densities in 35 mm dishes in control medium: 2, 10, 20, 100, 200, and 1000 cells/cm$^2$. Cells were harvested with 0.25% Trypsin at 7 and 14 days for counting using a hemacytometer. To analyze the cell kinetics, 10000 cells were plated in 35 mm dishes and were counted every two days for two weeks using the above technique.

Flow Cytometry: To determine the quantitative smooth muscle composition of the ADSC's, the cells were analyzed by flow cytometry using three markers: 1) an early smooth muscle marker, Alpha smooth muscle actin (ASMA); 2) an intermediate marker, Calponin (CAL); and 3) a late marker for smooth muscle, myosin heavy chain (MHC). Cytometry data was collected from cells from the three fat depots (in passage 2-4) that were grown in vitro for 6 to 7 weeks in either SMDS, SMSZ, or control medium (DMEM). Cell viability was assessed by using propidium iodide and samples were corrected for viability, nonspecific fluorescence, and autofluorescence. The number of positive events for each cell-specific marker was expressed as a percentage of the total PLA cell number.

Adipogenic Differentiation: Cells were plated in control medium at a concentration of 5000 cells/cm$^2$ until approximately 70% confluency, at which point the medium was changed to adipogenic differentiation medium. Cells were kept in this medium for 72 hours and then maintained in adipocyte maintaining medium for 11 more days, with medium changes every 2-3 days. The cells were analyzed for the presence of lipid-filled vacuoles through staining with Oil Red O (Sigma).

Osteogenic Differentiation: Cells were plated and induced in osteogenic differentiation medium using the same techniques as described supra for in adipogenic differentiation. After five weeks, osteogenesis was assessed qualitatively by von Kossa and alkaline phosphatase staining using the procedures described infra. The quantitative expression of alkaline phosphotase and calcium were analyzed.

Alkaline Phosphatase Activity: Cells in 6-well plates were rinsed in 1×PBS and incubated at 37° C. using a mixture of 200 µL of NBT/BCIP Stock Solution (from Genius Kit, Boehringer-Mannheim) plus 10 mL of 0.1 M Tris-HCl/0.1 M NaCl at pH 9.5. After color developed (approximately 30 minutes), the cells are gently washed with 1×PBS and postfixed with 4% paraformaldehyde for 5 minutes at room temperature, followed by rinsing with distilled water. Osteoblastic differentiation was detected by a positive red stain for alkaline phosphatase activity.

Von Kossa Staining for $Ca^{2+}$: Cells in 6-well plates were rinsed with 1×PBS and fixed with 0.1% gluteraldehyde in PBS (pH 7) for 15 minutes at room temperature. After washing twice with distilled water, cells were incubated in 5% silver nitrate for 30 minutes in the dark, also at room termperature. Cells were washed with distilled water and air-dried under ultraviolet lighting for 1 hour or until black color developed in areas of calcification. Cells were counterstained with 0.1% Eosin in ethanol for 3 minutes.

Smooth Muscle Differentiation: To characterize smooth muscle differentiation of the investigated ADSCs using immunohistochemistry cells were cultured in 24-well plates. To determine differentiation based on smooth muscle-related protein expression, cells were cultured in 100 mm$^2$ plates. Cells reaching 50% confluency in their respective plates were induced with either SMDS, SMDZ, or continued to grow with control medium. Cells were cultured for six weeks, and the media were replaced every 2-3 days.

Immunohistochemistry: The immunohistochemistry was performed using a commercial kit (R.T.U. VECTASTAIN® ABC Kit, Vector Laboratories, Burlingame, Calif.). Briefly, the cells were washed with 1×PBS, air dried, and then fixed with acetone/methanol 1:1 for 5 minutes. Blocking of the non-specific antibody binding sites was done by incubating the cells with 2.5% normal horse serum for one hour. The cells were then incubated with the primary antibody diluted in PBS overnight at 4° C. (see supra for antibodies and dilutions). After washing the cells three times with 1×PBS, the cells were incubated with the biotinylated secondary antibody for 30 minutes at room temperature. The cells were incubated with Vectastain R.T.U. Elite ABC Reagent for and additional 30 minutes at room temperature, and then stained for approximately 3-5 minutes using a DAB peroxidase substrate kit (Vector). Cells were counterstained using hematoxylin and examined using optical microscopy.

Western Blot: Cells were washed with 1×PBS and the proteins extracted by treating cells with lysis buffer for 10 minutes on ice at a concentration of $5 \times 10^7$ cells per 1 mL of buffer. 20 µg of protein was loaded and separated on SDS polyacrylamide gels and blotted onto nitrocellulose membranes using standard protocols.

Results: Differences in growth kinetics and clonal proliferation, with ADSCs originating in gonadal region of male subjects growing at faster rate than female cells were observed. In addition, although all cells could be differentiated into multiple cell types, different adipogenic region specific to the genders showed preferential differentiation to specific cell types.

In a separate experiment, to test these effects of gender in both growth kinetics were due to circulating steroid hormones as well as differentiation of ADSCs the following experiments were conducted:

ADSC from female adult rats were harvested and plated as previously described and plated at density and treated with DHT. (DHT: 5α-ANDROTAN-17β-OL3-ONE from Sigma, diluted in 100% EtOH). ADSC from male adult rats were harvested and plated as described supra and treated with estrogen.

Protocol for MTT for Estrogen and DHT Studies: Cultured cells are harvested using 0.25% trypsin and subsequently re-suspended in 10% cFBS (charcoal treated fetal bovine serum) phenol red-free DMEM w/1% L-glutamine and 1% antibiotic-antimycotic. Cells are seeded into 96-well plates at a density of $1 \times 10^4$ cells/cm$^2$. Once cells reach 60-70% confluency, they are starved using 0.5% cFBS phenol red-free DMEM (w/1% L-glutamine and 1% antibiotic-antimycotic) for 24 hours. Following starvation, cells are treated with 5% cFBS phenol red-free DMEM (w/1% L-glutamine and 1% antibiotic-antimycotic) with desired concentration of estrogen (estrogen was 17 β-Estradiol (Calbiochem, San Diego, Calif.), diluted in EtOH) or DHT (usually $1 \times 10^{-4}$ to $1 \times 10^{-12}$). Cell viability assay is performed by adding 20 µL of CellTiter 96® Aqueous reagent to each well and incubating the plate for 1-4 hrs in darkness at 37° C. The absorbance is recorded using a microplate reader at 490 nm.

Female rats were oophorectomized and divided in the following 2 groups. The first group was treated with weekly IM injections of cottonseed oil (control)(Sigma, MO). The second group was treated with weekly IM injections of 0.75 mg/kg of estradiol cypionate (Sterus laboratories, Inc., AZ).

The ADSCs from the three different fat depots are harvested as per the previous protocol and growth kinetics and differentiation experiments are similarly conducted and compared to normal male rats and female rats.

Experiment No. 9—Smooth Muscle Contraction In Vitro Assay

A mixture of 50% collagen solution (Vitrogen), 25% 4×DMEM with supplemented sodium bicarbonate prepared from powder (Gibco), ~5 µl volume of glass bead (120-150 µm soda lime microspheres in light blue color) were added to approximately $5 \times 10^5$ cells (smooth muscle cells differentiated from ADSCs, although other cell types were utilized as negative controls) to a total volume of 400 µl was prepared on ice. The slurry was transferred to a 24-well plate (with calculated resulting thickness of around 2 mm) and the gel was allowed to polymerize in the 37° C. incubator overnight. Appropriate cell culture medium was added the next day to supplement cell growth, e,.g., smooth muscle medium was added to smooth muscle cells or adipogenic medium was added to adipose cells. The gel was incubated again for another night.

The following day (2 days after casting the gel) the gel was partially released (i.e., about 280° around the circumference of the well) from the tissue culture well by gently pulling the gel away from the side of the well with a pipette. Carbachol (an acetylcholine agonist) was added to the partially released gel. Response to addition of the drug was monitored by use of a microscope connected to a real-time camera.

Murine NIH 3T3 (fibroblasts ) or undifferentiated PLA cells were run concurrently as controls.

Pictures were taken before the gel was released at marked fields. The gel was released with a pipette tip about 280° around the wall of the well. Pictures were taken every few minutes from this point. After the gel contraction from releasing the gel had been stabilized, the desired drugs were added and pictures were continued to be taken. Result were interpreted by measuring the change of distance between the beads over time. (keep them on the plate to keep gel from floating.)

The inventors discovered that releasing the gel at a later, rather than earlier stage maintained a relatively high tensional strength around the gel to all sides of the well. In contrast, in the floating gel model, the gel remained mechanically unloaded and the collagen fibrils were more random. The 2-step restained-release model was found to have maximal contraction (see Grinnell et al (1999) J. Biol. Chem. 274(2): 918, for a description of this model) and it was chosen to optimize detection for any contractions.

Results: Smooth muscle cells showed the predicted contractile response to the acetylcholine agonist Carbachol. In a separate experiment, an acetylcholine inhibitor (Atropine) was added prior to the addition of Carbachol which greatly reduced the contractile response. The controls (fibroblasts (NIH 3T3) or undifferentiated PLA) showed very weak response to Carbachol.

In a separate experiment, ADSMC contractile response to the β receptor agonist isoproterenol was tested. In a yet further experiment, blocking isoproterenol with its inhibitor Propranolol beforehand reduced the contractile response. Fibroblasts (NIH 3T3) or undifferentiated PLA had no response on smooth muscle contraction.

In a yet further experiment, the a receptor agonist Phenylephrine (α) was added to the gel and cells under the same conditions discussed above. Phenylephrine (α) was shown to contract gels. This experiment demonstrates that ADSC can be delivered in situ in a variety of formulations.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supercede any such material. The citation of any reference herein is not an admission that such reference is prior art to the present invention.

What is claimed is:

1. A method for inducing leiomyogenic differentiation of a purified adipose-derived stem cell (ADSC) comprising contacting the purified ADSC in vitro with an effective amount of a source of heparin thereby inducing leiomyogenic differentiation.

2. The method of claim 1, wherein the purified ADSC is obtained from a source selected from the group consisting of processed lipoaspirate, a substantially homogeneous population of ADSC, a clonal population of ADSC and a single, isolated ADSC.

3. The method of claim 1 or 2, further comprising contacting the purified ADSC with a source of laminin or a growth factor.

4. The method of claim 1 or 2, further comprising transplanting said ADSC into a tissue in a subject.

5. The method of claim 3, further comprising transplanting said ADSC into a tissue in a subject.

6. The method of claim 4, wherein the tissue comprises the gerintourinary tract of the subject.

7. The method of claim 5, wherein the tissue comprises the gerintourinary tract of the subject.

8. The method of claim 6, wherein the tissue comprises the bladder or urethra of the subject.

9. The method of claim 7, wherein the tissue comprises the bladder or urethra of the subject.

* * * * *

UNITED STATES PATENT AND TRADEMARK OFFICE
CERTIFICATE OF CORRECTION

| | | |
|---|---|---|
| PATENT NO. | : 7,531,355 B2 | Page 1 of 1 |
| APPLICATION NO. | : 11/192753 | |
| DATED | : May 12, 2009 | |
| INVENTOR(S) | : Larissa V. Rodríguez and Ben Wu | |

It is certified that error appears in the above-identified patent and that said Letters Patent is hereby corrected as shown below:

Column 1, lines 7-9, the paragraph which currently reads:

"This invention was made with Government support of Grand No. KD076198 and HD01400 awarded by the National Institutes of Health. Accordingly, the U.S. government has certain rights in this invention."

should be replaced with:

-- This invention was made with Government support of Grant No. DK076198 and HD01400 awarded by the National Institutes of Health. Accordingly, the U.S. government has certain rights in this invention. --

Signed and Sealed this

Fourth Day of August, 2009

JOHN DOLL
*Acting Director of the United States Patent and Trademark Office*

SEQUENCE LISTING

```
<160> NUMBER OF SEQ ID NOS: 14

<210> SEQ ID NO 1
<211> LENGTH: 17
<212> TYPE: DNA
<213> ORGANISM: Artificial
<220> FEATURE:
<223> OTHER INFORMATION: PCR Primer

<400> SEQUENCE: 1
atggccaaca agggtcc                                                      17

<210> SEQ ID NO 2
<211> LENGTH: 19
<212> TYPE: DNA
<213> ORGANISM: Artificial
<220> FEATURE:
<223> OTHER INFORMATION: PCR primer
```

-continued

```
<400> SEQUENCE: 2
atggcggacg aggccttag                                                  19

<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
agattgaaag gcgaagagca                                                 20

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
ggacgacctg gttgttgatt                                                 20

<210> SEQ ID NO 5
<211> LENGTH: 19
<212> TYPE: DNA
<213> ORGANISM: Artificial
<220> FEATURE:
<223> OTHER INFORMATION: PCR primer

<400> SEQUENCE: 5
atgtcctctg ctcacttca                                                  19

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
acccacaatg tccccatcta                                                 20

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
gtagatgggc acagtgtggg                                                 20

<210> SEQ ID NO 8
<211> LENGTH: 18
<212> TYPE: DNA
<213> ORGANISM: Artificial
<220> FEATURE:
<223> OTHER INFORMATION: PCR primer

<400> SEQUENCE: 8
cttcaaagag gtcaacag                                                   18

<210> SEQ ID NO 9
<211> LENGTH: 18
```

```
<212> TYPE: DNA
<213> ORGANISM: Artificial
<220> FEATURE:
<223> OTHER INFORMATION: PCR primer

<400> SEQUENCE: 9
cctcaatctc ctgagccc                                                  18

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
ttcaagccag cagtttcctt                                                20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
gtagctgctt gatggcttcc                                                20

<210> SEQ ID NO 12
<211> LENGTH: 19
<212> TYPE: DNA
<213> ORGANISM: Artificial
<220> FEATURE:
<223> OTHER INFORMATION: PCR primer

<400> SEQUENCE: 12
tttccgctcc tgcttctct                                                 19

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
tgatccacat ctgctggaag                                                20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
atggatgatg atatcgccgc                                                20
```